(12) United States Patent
Boppart et al.

(10) Patent No.: US 11,445,915 B2
(45) Date of Patent: Sep. 20, 2022

(54) COMPACT BRIEFCASE OCT SYSTEM FOR POINT-OF-CARE IMAGING

(71) Applicant: The Board of Trustees of the University of Illinois, Urbana, IL (US)

(72) Inventors: Stephen A. Boppart, Champaign, IL (US); Roshan I. Dsouza, Champaign, IL (US); Darold R. Spillman, Jr., Tuscola, IL (US); Paritosh Pande, Richland, WA (US); Guillermo L. Monroy, Burbank, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 93 days.

(21) Appl. No.: 16/520,037

(22) Filed: Jul. 23, 2019

(65) Prior Publication Data
US 2019/0343390 A1    Nov. 14, 2019

Related U.S. Application Data

(63) Continuation-in-part of application No. 15/811,999, filed on Nov. 14, 2017, now Pat. No. 10,401,141.
(Continued)

(51) Int. Cl.
*A61B 5/00* (2006.01)
*A61B 1/227* (2006.01)
(Continued)

(52) U.S. Cl.
CPC ............ *A61B 5/0066* (2013.01); *A61B 1/227* (2013.01); *G01B 9/02091* (2013.01);
(Continued)

(58) Field of Classification Search
CPC ..... A61B 5/0066; A61B 1/227; A61B 5/7257; G01B 9/02091; G01B 9/02041; G01N 21/4795
See application file for complete search history.

(56) References Cited

U.S. PATENT DOCUMENTS

| 7,586,618 B2 | 9/2009 | Marks et al. |
| 7,623,908 B2 | 11/2009 | Boppart et al. |

(Continued)

FOREIGN PATENT DOCUMENTS

WO    WO 02/088705 A2    11/2002

OTHER PUBLICATIONS

Heine Beta® 200 Fiber Optic Otoscope, 1 page.
(Continued)

*Primary Examiner* — David F Dunphy
(74) *Attorney, Agent, or Firm* — Sunstein LLP

(57) ABSTRACT

A detector for characterizing at least one of a middle ear fluid and a middle ear biofilm includes a handheld probe outputting near-infrared and visible light, an OCT system to obtain A-scans at a plurality of positions on a tympanic membrane, and a camera to obtain surface sub-images at the plurality of positions. A-scans and surface sub-images are synchronized and the surface sub-images are mosaicked to generate a surface image of the tympanic membrane. Cross-sectional scan images or a thickness map are generated from the synchronized A-scans and segmented to extract a plurality of specified features. The specified features are then classified to characterize at least one of the middle ear fluid and the middle ear biofilm. The detector, including handheld probe with camera, OCT system, and a laptop computer, is sized to fit into a handheld, portable, compact, foam-padded briefcase weighing less than 10 kg.

30 Claims, 10 Drawing Sheets
(7 of 10 Drawing Sheet(s) Filed in Color)

Related U.S. Application Data

(60) Provisional application No. 62/760,991, filed on Nov. 14, 2018, provisional application No. 62/765,267, filed on Aug. 20, 2018, provisional application No. 62/702,380, filed on Jul. 24, 2018, provisional application No. 62/428,573, filed on Dec. 1, 2016.

(51) Int. Cl.
  G01B 9/02 (2022.01)
  G01N 21/47 (2006.01)
  G01B 9/02091 (2022.01)

(52) U.S. Cl.
  CPC ........ G01N 21/4795 (2013.01); A61B 5/7257 (2013.01); G01B 9/02041 (2013.01)

(56) References Cited

U.S. PATENT DOCUMENTS

| | | | |
|---|---|---|---|
| 7,725,169 B2 | 5/2010 | Boppart et al. | |
| 7,787,129 B2 | 8/2010 | Zysk et al. | |
| 7,831,090 B1 | 11/2010 | Krishnan et al. | |
| 8,115,934 B2* | 2/2012 | Boppart | G01B 9/02014 356/479 |
| 2003/0082104 A1 | 5/2003 | Mertelmeier | |
| 2003/0123713 A1 | 7/2003 | Geng | |
| 2004/0181128 A1 | 9/2004 | Masters | |
| 2006/0274973 A1* | 12/2006 | Mohamed | G06K 9/4633 382/281 |
| 2006/0276709 A1 | 12/2006 | Khamene et al. | |
| 2009/0185191 A1 | 7/2009 | Boppart et al. | |
| 2010/0094137 A1 | 4/2010 | Furlong et al. | |
| 2010/0149183 A1* | 6/2010 | Loewke | G06K 9/32 345/424 |
| 2013/0060131 A1 | 3/2013 | Oghalai et al. | |
| 2013/0208240 A1* | 8/2013 | Sharma | G06T 7/11 351/206 |
| 2013/0222566 A1 | 8/2013 | Murase | |
| 2013/0253313 A1* | 9/2013 | Kang | A61B 1/00165 600/425 |
| 2015/0062590 A1* | 3/2015 | Bagherinia | G06T 7/10 356/479 |
| 2015/0351606 A1 | 12/2015 | Ruppersberg et al. | |
| 2015/0381968 A1 | 12/2015 | Arora et al. | |
| 2016/0007840 A1 | 1/2016 | Boppart et al. | |
| 2016/0228208 A1 | 8/2016 | Samsonov et al. | |
| 2018/0055355 A1 | 3/2018 | Sarunic et al. | |
| 2018/0325601 A1 | 11/2018 | Mak et al. | |

OTHER PUBLICATIONS

Welch Allyn Macro View™ sell sheet, 2 pages (2008).
American Academy of Family Physicians, "Otitis Media With Effusion," Pediatrics, vol. 113, No. 5, pp. 1412-1429, May 2004.
Bay, et al., "Speeded Up Robust Features," Computer Vision and Image Understanding, vol. 110, pp. 346-359, 2008.
Boppart, "Finding Bugs in your Ear: Clinical Imaging of Middle-Ear Infections and Biofilms using OCT," Conference on Lasers and Electro-Optics, OSA, 2 pages, May 10, 2015.
Can et al., "A feature-based, robust, hierarchical algorithm for registering pairs of images of the curved human retina," Pattern Analysis and Machine Intelligence, IEEE Transactions on, vol. 24, pp. 347-364, 2002.
Chanwimaluang et al., "Hybrid retinal image registration," IEEE Trans. Inf. Tech, in Biomedicine, vol. 10, pp. 129-142, 2006.
Hall-Stoodley et al., "Direct Detection of Bacterial Biofilms on the Middle-Ear Mucosa of Children with Chronic Otitis Media," JAMA, vol. 296, No. 2, pp. 202-211, Jul. 2006.
Hubler et al., "Real-time automated thickness measurement of the in vivo human tympanic membrane using optical coherence tomography," Quantitative Imaging in Medicine and Surgery, vol. 5, pp. 69-77, 2015.
Jung et al., "Handheld Optical Coherence Tomography Scanner for Primary Care Diagnostics," IEEE T. Bio-Med. Eng., vol. 58, No. 3, pp. 741-744, Mar. 2011.
Jupeng et al., "A robust feature-based method for mosaic of the curved human color retinal images," IEEE International Conf. on Biomedical Engineering and Informatics, vol. 1, pp. 845-849, 2008.
Li et al., "Automatic montage of SD-OCT data sets," Opt. Exp., vol. 19, pp. 239-248, 2011.
Lowe, "Object recognition from local scale-invariant features," Computer Vision, pp. 1150-1157, 1999.
Marks et al., "Inverse scattering for frequency-scanned full-field optical coherence tomography," J. Opt. Soc. Am. A, vol. 24, No. 4, pp. 1034-1041, Apr. 2007.
Monroy et al., "Non-invasive Depth-Resolved Optical Measurements of the Tympanic Membrane and Middle Ear for Differentiating Otitis Media," The Laryngoscope, vol. 125, pp. E276-E282, 2015.
Ahmad et al., Cross-correlation-based image acquisition technique for manually-scanned optical coherence tomography, Optics Express, vol. 17, No. 4, 13 pages, 2010.
Podleanu, "Optical coherence tomography," Journal of Microscopy, 11 pages, 2012.
Nguyen et al., "Noninvasive in vivo optical detection of biofilm in the human middle ear," Proc. Nat. Acad. Sci., vol. 109, No. 24, pp. 9529-9534, Jun. 2012.
Nguyen et al., "Non-invasive optical interferometry for the assessment of biofilm growth in the middle ear," Biomedical Optics Express, vol. 1, No. 4, 13 pages, 2010.
Pitris et al., "High-Resolution Imaging of the Middle Ear with Optical Coherence Tomography: A Feasibility Study," Arch. Otolaryngol., vol. 127, pp. 637-642, Jun. 2001.
Pol et al., "Biomedical image mosaicking: A review," in Communication and Computing Systems: Proc. Int. Conf,. on Comm. and Computing Systems, ICCS—2016, Prasad et al., ed., pp. 155-157, 2017.
Reed et al., "Gradient-index fiber-optic microprobes for minimally invasive in vivo low-coherence interferometry," Opt. Lett., vol. 27, No. 20, pp. 1794-1796, Oct. 2002.
Shelton et al., "Optical coherence tomography for advanced screening in the primary care office," J. Biophotonics, pp. 1-9, Apr. 2013.
Shelton et al., "Quantitative Pneumatic Otoscopy Using a Light-Based Ranging Technique," Journal of the Association for Research in Otolaryngology, vol. 18, No. 4, pp. 555-568, Jun. 26, 2017.
Szeliski, "Image alignment and stitching: A tutorial," Foundations and Trends in Computer Graphics and Vision, vol. 2, pp. 1-104, 2006.
Takata et al., "Evidence Assessment of the Accuracy of Methods of Diagnosing Middle Ear Effusion in Children with Otitis Media with Effusion," Pediatrics, vol. 112, No. 6, pp. 1379-1387, Dec. 2003.
Van der Jeught et al., "Full-field thickness distribution of human tympanic membrane obtained with optical coherence tomography," J. Association for Research in Otolaryngology, vol. 14, pp. 483-494, 2013.
Wang et al., "A three-dimensional gap filling method for large geophysical datasets: Application to global satellite soil moisture observations," Environmental Modelling & Software vol. 30, pp. 139-142, Apr. 2012.
Westphal et al., "Correction of geometric and refractive image distortions in optical coherence tomography applying Fermat's principle," Optics Express, vol. 10, No. 9, pp. 397-404, May 6, 2002.
Xi et al., "High-resolution three-dimensional imaging of biofilm development using optical coherence tomography," J. Biomed. Opt., vol. 11, No. 3, pp. 134001-1-134001-6, May/Jun. 2006.
Yang et al., "Covariance-driven mosaic formation from sparsely overlapping image sets with application to retinal image mosaicking," Proceedings of the 2004 IEEE Computer Society Conference on Computer Vision and Pattern Recognition, 6 pages, 2004.
Zysk et al., "Computational methods of analysis of human breast tumor tissue in optical coherence tomography images," J. Biomed. Opt., vol. 11, No. 5, pp. 054015-1-054015-7, Sep./Oct. 2006.

(56) References Cited

OTHER PUBLICATIONS

European Patent Office as the, International Search Report and Written Opinion of the International Searching Authority, International Searching Authority, Authorized Officer: Desirée Klug, PCT/US2019/043062, dated Oct. 17, 2019, 17 pages.

Fastenberg et al., "Biofilms in chronic rhinosinusitis: Pathophysiology and therapeutic strategies," World Journal of Otorhinolaryngology—Head and Neck Surgery, vol. 2, pp. 219-229, (2016).

Pande et al., "Sensor-Based Technique for Manually Scanned Hand-Held Optical Coherence Tomography Imaging," J. Sensors, vol. 2016, 8154809, 8 pages (2016).

Pande et al., "A Mosaicking Approach for In Vivo Thickness Mapping of the Human Tympanic Membrane Using Low Coherence Interferometry," J. Assoc. for Research in Otolaryngology, vol. 17, pp. 403-416 (2016).

Pande et al., "Low-cost hand-held probe for depth-resolved low-coherence interferometry," Biomed. Opt. Express, vol. 8, pp. 338-348 (Jan. 1, 2017).

Kim et al., "Design and implementation of a low-cost portable OCT system," Biomed. Opt. Express, vol. 9, 314842, 12 pages (2018).

Won et al., "Pneumatic low-coherence interferometry otoscope to quantify tympanic membrane mobility and middle ear pressure," Biomed. Opt. Express, vol. 9, pp. 397-409 (2018).

Monroy et al., "Noninvasive in vivo optical coherence tomography tracking of chronic otitis media in pediatric subjects after surgical intervention," Journal of Biomedical Optics, vol. 22, 11, 12 pages (2017).

Monroy et al., "Non-invasive optical assessment of viscosity of middle ear effusions in otitis media," Journal of Biophotonics, vol. 10, pp. 394-403, (2016).

Monroy et al., "Direct analysis of pathogenic structures affixed to the tympanic membrane during chronic otitis media," Otolaryngology—Head and Neck Surgery, vol. 159(1), pp. 117-126 (2018).

Zhao, et al., "Rapid diagnosis and differentiation of microbial pathogens in otitis media with a combined Raman spectroscopy and low-coherence interferometry probe: Toward in vivo implementation," Journal of Biomedical Optics vol. 21, 107005, 9 pages, (2016).

Nguyen, et al., "Investigation of bacterial biofilm in the human middle ear using OCT techniques and acoustic measurements," Hearing Research, vol. 301, 3 pages, (Jul. 2013).

Breiman, "Random Forests," Machine Learning, vol. 45, pp. 5-32, (2001).

Dsouza et al., "Economical and compact briefcase spectral-domain optical coherence tomography system for primary care and point-of-care applications," J. Biomed. Opt., vol. 23(9), 12 pages, Sep. 24, 2018.

* cited by examiner

COMPACT BRIEFCASE OCT SYSTEM FOR POINT-OF-CARE IMAGING

The present application is a continuation-in-part of U.S. patent application Ser. No. 15/811,999, filed Nov. 14, 2017, entitled "Method and Apparatus for Obtaining a Three-Dimensional Map of Tympanic Membrane Thickness", which claims priority to U.S. Provisional Patent Application Ser. No. 62/428,573, filed Dec. 1, 2016. The present application further claims priority to U.S. Provisional Patent Application Ser. No. 62/702,380, entitled "Compact Briefcase OCT System for Point-of-Care-Imaging" and filed Jul. 24, 2018; 62/765,267, entitled "Middle Ear Feature Detector" and filed Aug. 20, 2018; and 62/760,991, entitled "Compact Briefcase OCT System for Point-of-Care-Imaging" and filed Nov. 14, 2018. All of the foregoing applications are incorporated in their entirety herein by reference.

This invention was made with government support under grants RO1CA213149 and R01EB013723 awarded by the National Institutes of Health. The government has certain rights in the invention.

TECHNICAL FIELD

The present invention relates to apparatus and methods for medical tomographic imaging, and, more particularly, for imaging of an internal volume of an ear to identify pathological abnormalities.

BACKGROUND

Otitis media (OM) is a common infection of the middle ear in children, with combined direct and indirect annual costs estimated to be (US$) 4 billion. OM is a broad term for inflammation of the ear, which is further subdivided into specific disease states. OM with effusion (OME) is a thought to be sterile accumulation of fluid within the middle ear cavity (MEC) that may form as a result of an unrelated upper respiratory infection. Alternatively, an ear infection can become a painful episode of acute OM (AOM), which may or may not include purulent and infected fluid. In either case, fluid accumulation may lead to hearing loss and speech and language developmental delays. Treatment for AOM is one of the most common reasons for children to be prescribed and overprescribed antibiotics.

If three or more episodes of AOM occur within 6 months, or four within one year, the infection can develop into recurrent acute OM (RAOM). Similarly, when middle ear fluid persists for 3 months or longer, this can develop into chronic OME (COME). The surgical placement of tympanostomy tubes (TT) can be used to treat these conditions. As such, TT placement is one of the most common outpatient procedures performed under anesthesia for children. It has been theorized that middle ear biofilms play a significant role in the persistence of RAOM and COME. Fastenberg et al., "*Biofilms in chronic rhinosinusitis: Pathophysiology and therapeutic strategies,*" *World Journal of Otorhinolaryngology—Head and Neck Surgery*, vol. 2, pp. 219-29, (2016), have shown that biofilms are collections of bacteria that have altered genetic expression profiles compared to their planktonic counterparts. A self-excreted exopolymeric matrix encapsulates the bacteria and affords a microenvironment that promotes increased bacterial resistance to antibiotics and host immune system activity. Biofilm-mediated infections in the ear, in other regions of the upper respiratory tract, as well as in the urinary tract and on implanted catheters and prosthetics, are difficult to treat.

To effectively treat patients diagnosed with OM, optimized and up to date treatment protocols aim to provide recommended best practices for antibiotic prescription and TT surgery by integrating evidence-based medicine though a systematic review of past studies and data. To diagnose OM, physicians typically utilize a standard otoscope to assess the ear drum, or tympanic membrane (TM). Otoscopes provide illumination and magnification of the TM and qualitative interpretation of visual indicators related to OM infection, including the coloration, transparency, and presence of middle ear fluid. Expert otolaryngologists intimately familiar with OM have an estimated diagnostic accuracy of approximately 70% using otoscopy, although early career physicians remain unquantified. Given the difficulty in properly diagnosing OM, AOM is frequently misdiagnosed. These treatment protocols are designed with this uncertainty in mind, and aim to reduce antibiotic overprescription and mitigate antibacterial resistance proliferation. Despite these efforts, the prescription and distribution of antibiotics remains high.

Various tools, such as tympanometry, acoustic reflectometry, and pneumatic otoscopy, can assess the middle ear using functional metrics. Qualitative assessment of tympanometry or acoustic reflectometry can indicate if middle ear fluid or TM perforations are present, although the estimated diagnostic accuracy for either device is insufficient for diagnosis alone and is often recommended that these be used in conjunction with otoscopy for a more complete assessment of infection status. Pneumatic otoscopy is performed with a modified otoscope that adds an insufflation bulb and speculum tip that seals the ear canal to allow for pressure modulation and observation of any TM deflection, which qualitatively can be used to determine fluid presence or altered middle ear pressure. Pneumatic otoscopy is recommended as the gold standard for OM assessment, and when used properly has an improved diagnostic sensitivity of 94%. However, it is difficult to utilize properly and is often not used in practice. Overall, there is an unmet need for a tool and methodology that provides a straightforward and quantitative assessment of middle ear pathology for a consistent and reliable diagnosis for OM.

To date, identification of otitis media (OM) has required visual inspection by trained personnel of the ear itself, using an otoscope, or of images derived from the ear using one or more of a variety of imaging modalities. There are clear advantages to a capability to derive measures of middle ear infection without the involvement of an expert.

Optical coherence tomography (OCT) is a cross-sectional imaging modality which collects backscattered near-infrared light from the specimen. OCT has been explored for its potential capability of being used in clinics for non-invasive and high-resolution real-time imaging. The two main variants of OCT systems are time-domain (TD) OCT and Fourier-domain (FD) OCT. TD-OCT systems operate by scanning a reference mirror at a constant velocity, but have limited scan rates and sensitivity. FD-OCT systems acquire depth-resolved information without moving the reference mirror. Furthermore, FD-OCT systems are further classified as spectral-domain (SD) OCT where depth-resolved information is obtained by a spectrometer, and swept-source (SS) OCT which uses a tunable light source and detector to measure interference signal as a function of time. Significant developments in improving OCT over the past two decades have revolutionized clinical diagnostic applications.

OCT is one possible tool that can quantitatively assess the TM and adjacent middle ear space for OM. OCT operates using a similar principle as ultrasound imaging, detecting back-reflections of near infrared light scattering from within tissue, and provides high-spatial-resolution images of tissue at the micrometer scale. Cross-sectional (B-mode or B-scan) images, which consist of multiple adjacent A-lines (A-scans or depth-scans) acquired as the optical beam is scanned across tissue. The clinical relevance of this tool and related challenges in middle ear imaging is currently being explored. Biofilms have been known to inhabit the MEC during OM infection. The ability of OCT imaging to identify middle ear fluid has been previously demonstrated, and more recently biofilms that are adhered to the TM during chronic or recurrent acute OM. FIG. 9 demonstrates representative cross-sectional OCT B-mode and radial A-line data from pediatric human subjects with these features. Yet, two significant barriers for translation of this technology remain. First, there are no clinical diagnostic guidelines or criteria to assess OCT images of the TM and middle ear for signs of OM. And similarly, any existing studies that have employed OCT for OM assessment have utilized experts familiar with middle ear imaging, OM, and OCT to interpret and correlate OCT data to currently accepted clinical markers of OM. To further translate this technology, there is a need for diagnostic criteria to be defined for OCT images of OM, and employed without the regular involvement of an expert reader, particularly as the cost of this technology is reduced and optimized for use by healthcare providers. Moreover, use in primary care and point-of-care applications would typically require readily portable instrumentation with a hand-scannable probe.

However, while hand scanning of a probe requires 3-D free-hand registration of data obtained at successive probe positions, the problem of 3-D free-hand registration has been a vexing one in fields of medical imaging that use surface-penetrating technologies such as OCT and ultrasound. One solution has been the identification of landmarks and post-acquisition registration; however a real-time solution has eluded researchers in the field until now. Algorithms that allow recovery of B-mode images (two-dimensional cross-sectional images) from 3-D free hand A-scans (depth-resolved linear backscatter profiles) are taught for the first time in accordance with the present invention.

Earlier work on free-hand tomographic scanning that falls within the prior art has included both sensorless techniques based on cross-correlation, as described, for example, by Ahmad et al., "*Cross-correlation-based image acquisition technique for manually-scanned optical coherence tomography,*" *Opt. Express*, vol. 17, pp. 8125-36 (2009) (Hereinafter, "Ahmad 2009"), incorporated herein by reference in its entirety, and sensor-based techniques that actively monitor position and/or motion of the probe, based on speckle tracking, or otherwise, as described by Pande et al., "*Sensor-Based Technique for Manually Scanned Hand-Held Optical Coherence Tomographic Imaging,*" *J. Sensors*, vol. 2016, U.S. Pat. No. 8,154,809 (2016).

Another prior art approach over which the present teachings constitute a conceptual advance is the technique described by Pande et al., "*A Mosaicking Approach for In Vivo Thickness Mapping of the Human Tympanic Membrane Using Low Coherence Interferometry,*" *J. Assoc. for Research in Otolaryngology*, vol. 17, pp. 403-16 (2016) (hereinafter, "Pande 2016"). Pande 2016 used an optical image co-aligned with the OCT system, and an affine transformation as the motion model, with parameters of the transformation matrix chosen by optimizing mutual information (MI) as the metric of similarity between two images.

None of the prior art 3-D freehand OCT techniques, however, was capable of guiding a user, holding an OCT probe, to effectively oversample regions of interest and position the probe within a specified range above a fiducial surface. That has been made possible only in accordance with the teachings of the present invention, described in detail below.

Diagnosis of infections and formation of biofilms within the middle ear requires more than measurement of tympanic membrane (TM) thickness, using, as it does, a suitcase of measures described below in accordance with the present invention. Prior art concepts, while suitable for thickness measurement, do not suffice for the detection of pathological features described herein, for which the new concepts of the present invention are advantageously suited.

Globally, researchers are developing cost-effective and mobile OCT systems based on both TD-OCT and FD-OCT platforms with unique detection/illumination schemes. Pande et al., "*Low-cost hand-held probe for depth-resolved low-coherence interferometry,*" *Biomed. Opt. Express*, vol. 8, pp. 338-48 (Jan. 1, 2017, hereinafter, "Pande 2017"), demonstrated the development of a compact TD-OCT within a handheld low-coherence interferometry (LCI) system. To the best of the applicants' knowledge, all portable OCT systems in the prior art, such as the hand-held probe described by Pande 2017, require on-board mechanical scanning by means of a galvanometer, or otherwise, to achieve B-mode coverage of a region of interest. This adds to the cost and complexity of the resulting systems. A portable OCT system described by Kim et al., "*Design and implementation of a low-cost portable OCT system,*" *Biomed. Opt. Express*, vol. 9, 314842 (2018), falls within the same category.

SUMMARY OF THE EMBODIMENTS

In accordance with one embodiment of the invention, a detector is provided for characterizing at least one of a middle ear fluid and a middle ear biofilm. The detector may include a handheld probe for directing an output of a broadband source of near-infrared radiation and a source of visible light onto a surface region of a tympanic membrane (TM) within an ear of a human. The handheld probe may also have a visible light camera. The detector may further include an OCT system adapted to obtain A-scans at a plurality of randomly distributed positions in the surface region as the handheld probe is manually scanned with no lateral scanning mechanism. The detector may also include at least one processor. The at least one processor may be configured to concurrently acquire A-scans from the OCT system and visible light surface sub-images of the surface region of the TM from the camera at the plurality of randomly distributed positions and perform mosaicking of the surface sub-images to obtain a mosaicked surface image in real time. The at least one processor may also be configured to synchronize the obtained A-scans with the surface sub-images by making use of the mosaicked surface image to generate at least one of cross-sectional scan images of a volume behind the TM within a middle ear space and a thickness map of the TM. The processor may further be configured to segment the at least one of the cross-sectional scan images and the thickness map to extract a plurality of specified features of the at least one of the volume behind the TM and the thickness map of the TM. The processor may also be configured to characterize at least one of the middle ear fluid and the middle ear biofilm by classifying the specified features.

In related system and method embodiments of the present invention, the plurality of specified features may include at least one OCT-derived feature such as of optical thickness, standard deviation of peak-position location, mean of peak width, standard deviation of peak width, mean peak prominence, standard deviation of peak prominence, total number of peaks, optical attenuation maximum, mean value in depth of optical attenuation, attenuation sum over peak-detected depth, Fourier width of central peak, or central Fourier peak prominence.

In yet other related embodiments, the OCT system may include a fiber optic Michelson interferometric configuration. The OCT system may also be a time-domain, spectral domain, or swept-source OCT system. The classifying may be the result of a random-forest classifier.

In another related embodiment of the present invention, the at least one processor is further configured to generate a diagnostic prediction indicating a presence and type of otitis media as a function of the characterizing the at least one of the middle ear fluid and the middle ear biofilm. In a further embodiment, the classifying may also include classifying clinical data of the human together with the plurality of specified features.

In other related embodiments of the invention, the at least one processor may also be configured to median filter the cross-sectional scan images of the volume behind the TM. In further embodiments, the mosaicking may include cross-correlating the surface sub-images, and the broadband source of near-infrared radiation may have a center wavelength of 840 nm and a bandwidth of 50 nm.

In accordance with an alternative embodiment of the present invention, a detector system is provided including a handheld briefcase with foam padding. The system may further include a handheld probe for directing an output of a broadband source of near-infrared radiation and a source of visible light onto a surface region. The handheld probe may also have a visible light camera. The system may further include an optical coherence tomography (OCT) system adapted to obtain A-scans at a plurality of randomly distributed positions in the surface region as the handheld probe is manually scanned with no lateral scanning mechanism. The system may also include a computing device having at least one processor. The at least one processor may be configured to concurrently acquire A-scans from the OCT system and visible light surface sub-images of the surface region from the camera at the plurality of randomly distributed positions and perform mosaicking of the surface sub-images to obtain a mosaicked surface image in real time. The at least one processor may also be configured to synchronize the obtained A-scans with the surface sub-images by making use of the mosaicked surface image to generate at least one of a cross-sectional scan images of a volume behind the surface region and a thickness map of the surface region. The foam padding may be configured to securely and immovably contain the handheld probe, the OCT system, and the computing device. The handheld briefcase containing the foam padding, the handheld probe, the OCT system, and the computing device may weigh less than 10 kilograms.

In a related embodiment of the invention, the briefcase may further include a power outlet. In yet another embodiment, the OCT system may include a spectrometer with a line-scan camera having a line rate of at least 10 kHz. In a further related embodiment of the invention, the computing device may be a laptop computer.

In accordance with another alternative embodiment of the present invention, a method is provided to obtain at least one of real-time three-dimensional images and a thickness map of tissue. The method may include directing the output of a broadband source of near-infrared radiation and a source of visible light via a handheld probe onto a surface region of a tympanic membrane within an ear of a human. The method may further include manually scanning the handheld probe to obtain optical coherence tomography A-scans at a plurality of randomly distributed positions on the surface region. The method may also include concurrently acquiring, by a visible light camera in the handheld probe, surface sub-images of the surface region of the TM at the plurality of randomly distributed positions. The method may further include mosaicking the surface sub-images to obtain a mosaicked surface image in real time. The method may include synchronizing the obtained OCT A-scans with the surface sub-images by making use of the mosaicked surface image to derive at least one of cross-sectional scan images of a volume behind the TM within a middle ear space and a thickness map of the TM.

In a related embodiment of the invention, the OCT A-scans may include at least one of time-domain, spectral-domain, and swept-source OCT A-scans.

In another related embodiment, the provided method may further include segmenting the at least one of the cross-sectional scan images and the thickness map to extract a plurality of specified features of at least one of a volume behind the TM within a middle ear space and the thickness map. The method may also include classifying the plurality of specified features to characterize at least one of a middle ear fluid and a middle ear biofilm. The provided method may further include median filtering the cross-sectional scan images. The mosaicking may include cross-correlating the surface sub-images.

In another related embodiment, the provided method may further include generating a diagnostic prediction indicating a presence and type of otitis media as a function of characterizing the least one of the middle ear fluid and the middle ear biofilm.

In accordance with yet another alternative embodiment of the invention, a detector is provided for detecting at least one of a middle ear biofilm and a middle ear fluid. The detector may include a handheld source of near-infrared radiation for illuminating tissue within an ear of a human. The detector may also include a spectral domain optical coherence tomography (OCT) system adapted to obtain cross-sectional scan images of the tissue. The detector may further have a median filter, comprising a square kernel and a lateral window, adapted to filter the cross-sectional scan images of the tissue. The detector may also have at least one processor adapted to segment the cross-sectional scan images of the tissue and extract a plurality of specified features of the tissue. The detector may further include a classifier for identifying at least one of the middle ear biofilm and the middle ear fluid by classifying the plurality of specified features.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing features of embodiments will be more readily understood by reference to the following detailed description, taken with reference to the accompanying drawings, in which.

DETAILED DESCRIPTION OF SPECIFIC EMBODIMENTS

Figure 1:
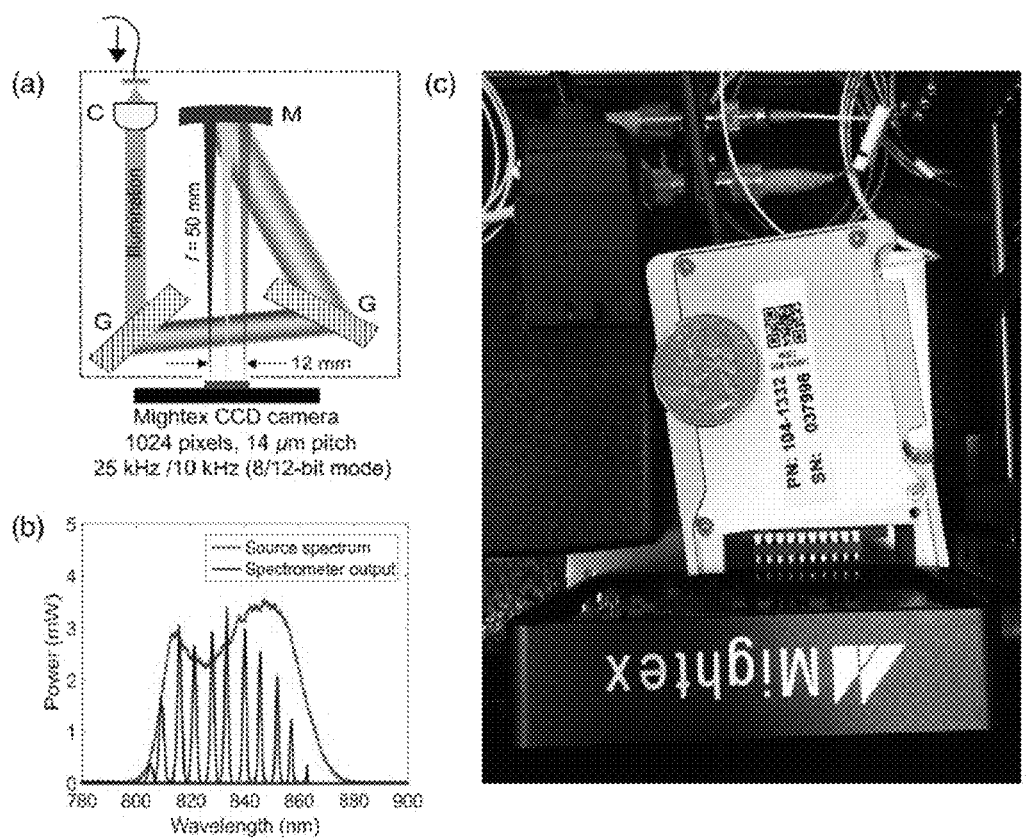
FIG. 1 depicts a compact, high-resolution spectrometer in accordance with an embodiment of the invention.

Definitions: Unless defined otherwise or required by context, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

The term "image" shall refer to any multidimensional representation, whether in tangible or otherwise perceptible form, or otherwise, whereby a value of some characteristic (amplitude, phase, etc.) is associated with each of a plurality of locations corresponding to dimensional coordinates of an object in physical space, though not necessarily mapped one-to-one thereon. Thus, for example, the graphic display of the spatial distribution of some field, either scalar or vectorial, such as brightness or color, constitutes an image. So, also, does an array of numbers, such as a 3D holographic dataset, in a computer memory or holographic medium. Similarly, "imaging" refers to the rendering of a stated physical characteristic in terms of one or more images.

The terms "object," "sample," and "specimen" shall refer, interchangeably, to a tangible, non-transitory physical object capable of being rendered as an image.

The word "detector" has two meanings that are evident from the context in which the word is used. In one sense, the word "detector" refers to a system for identifying the presence of a specified element or condition. In a second sense, "detector" refers to a device for generating an electronic detector signal on the basis of electromagnetic radiation impinging thereupon.

When used to modify terms such as "beam," "pulse," etc., the terms "sample" and "signal" are used herein interchangeably.

The term "scattering medium," as used herein and in any appended claim, shall mean a medium in which an incident electromagnetic wave, of a wavelength range pertinent to the context under discussion, shall be characterized by a mean free path to scatter that is substantially shorter than the dimension of the medium in the propagation direction of the incident electromagnetic wave.

The term "scattering biological tissue," as used herein and in any appended claim, shall mean an organized ensemble of interconnected cells of an organism that has the optical properties associated with a scattering medium, as defined above.

The term "low-coherence" (or "broadband," as used interchangeably herein) applies to a source of illumination for which the coherence length is shorter than 30 μm, and/or for which $\Delta k/k_0$ is at least 10%, with $k_0$ denoting the central wavenumber of the spectrum illuminating the sample, while $\Delta k$ denotes the range of illuminating wavenumbers. It is to be understood that, within the scope of the present invention, the wavelength of the source need not be fixed in time, indeed, the wavelength of the source may be swept in time.

The term "canvas" refers to a predefined zero matrix used for concatenation of successively registered images for stitching.

Embodiments of the present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

Overview

By way of introduction, the embodiments of the present invention may provide a compact, portable, briefcase SD-OCT system with a handheld probe for ready use in primary care and/or point-of-care settings. Such a fully self-contained OCT system includes all optical hardware, handheld probe, and a laptop computer in a compact and handheld briefcase. This design incorporates manual lateral scanning in real-time to reveal cross-sectional structural information, coupled with and synchronized to the visualization of tissue surfaces by mosaicking images. The manual lateral scanning approach not only reduces system cost and weight, but also facilitates cross-sectional imaging over larger areas of tissue, and subsequently larger fields-of-view (FOV), which otherwise would be restricted with mechanical scanning methods.

A self-contained briefcase OCT preferably contains associated optical hardware, including light source, spectrometer, hand-held probe, and a computing device such as a laptop computer. The laptop computer has at least one processor and is configured to perform tasks including, but not limited to, OCT acquisition, surface image acquisition, image synchronization, mosaicking, segmentation, and classification as described in further detail below. Additionally, this system utilizes unique real-time mosaicking of surface video images that are synchronized with rapid A-scan acquisition to eliminate the need for lateral scanning hardware, and enable the construction of cross-sectional B-mode images over extended lateral distances.

Such a portable, low-cost, briefcase OCT system as enabled by teachings of the present invention may advantageously serve for use in primary care and point-of-care applications, in various medical diagnostics, for biological field work (specifically to diagnose middle ear infection), and for non-destructive testing of materials. Measurements using such a system may be performed non-invasively through tissue or other interfaces/layers of material provided they are optically transparent for OCT imaging.

Compact OCT Spectrometer

The spectrometer in a conventional SD-OCT system is one of the most critical components where light is dispersed onto a line scan camera to spectrally separate and measure the interferometric signal. While commercially available spectrometers demonstrate excellent performance, they are often bulky and expensive, limiting their use in low-cost applications. In a preferred embodiment of the invention, a spectrometer available from Ibsen Photonics, Denmark is modified by substitution of a detector. This spectrometer has a spectral bandwidth of 50 nm (810-860 nm) with high spectral resolution (0.08 nm). The detector employed may be, for example, a USB 2.0 charge-coupled device (CCD) line-scan camera supplied by Mightex of North York, Ontario, Canada. This camera can operate in either an 8- or 12-bit mode, and provides a line rate of either 25 kHz or 10 kHz. In one example, this camera was operated at a 10 kHz acquisition rate and in 12-bit mode.

A schematic of the modified spectrometer is shown in FIG. 1(a). The light from the grating had a beam spread of 12 mm and was matched closely to the detector array size (14.3 mm). FIG. 1(b) shows the measured source spectrum versus the spectrometer output, confirming that the entire source spectrum was detected by the spectrometer sensor. The final dimensions of the modified spectrometer were approximately 90 mm height×90 mm width×70 mm depth.

Figure 2:
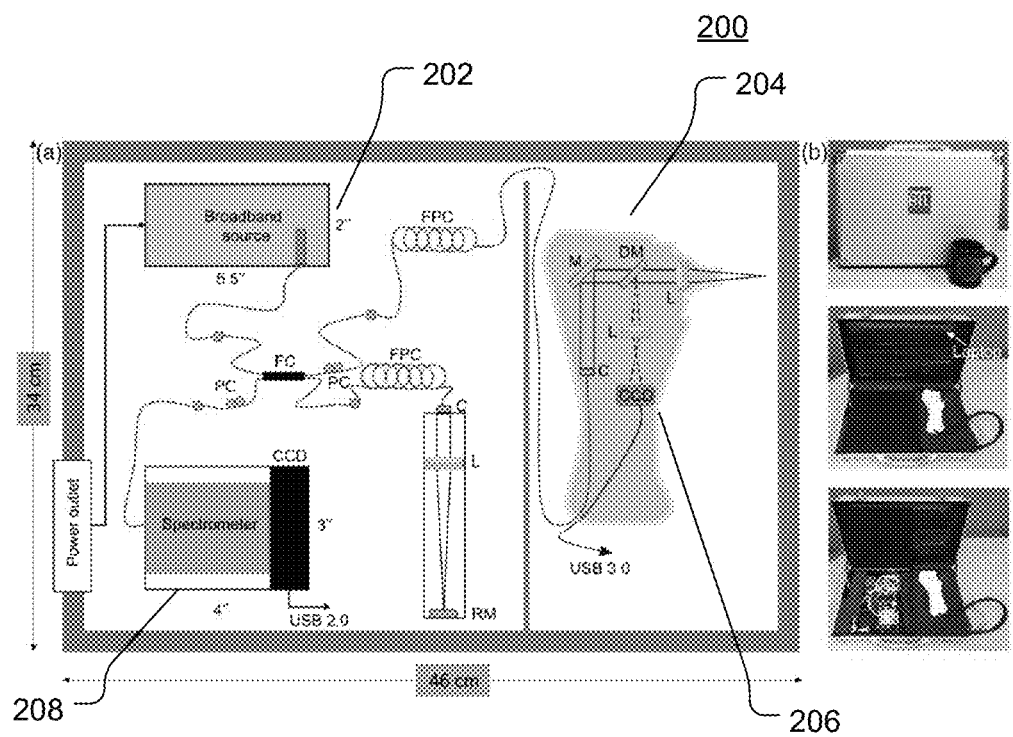
FIG. 2 shows a compact briefcase OCT system in accordance with an embodiment of the invention.

One design of an OCT system 200 in accordance with an embodiment of the present invention fits into a standard handheld briefcase (34 cm height×46 cm width×13 cm depth) in order to be compact, easily portable, and able to be used for point-of-care applications. FIG. 2 shows an exemplary briefcase (FIG. 2(b)) and the arrangement of the components of the OCT system 200 within (FIG. 2(a)). Additionally, this briefcase enclosure also protects all components during transportation. The handheld, compact briefcase also includes a computing device, such as a laptop computer, and weighs only 20 pounds, i.e. less than 10 kilograms. The SD-OCT system 200 is based on a fiber optic Michelson interferometer configuration. Near-infrared light is generated by a broadband near-infrared source 202, such as an uncooled superluminescent diode, which may be obtained from Exalos AG of Zurich, Switzerland. In a preferred embodiment, the source has a center wavelength of 840 nm, full-width-half-maximum (FWHM) bandwidth of 50 nm, and output power of 3.4 mW). Near-infrared light is guided from the source into one port of a 2×2 fiber coupler (FC) and split into the reference and sample arms.

In the sample arm, a handheld probe 204 is connected via a fiber optic cable. The handheld probe utilizes a mirror and a focusing lens (f=60 mm, for example) to focus the beam on a sample. A compact high-speed USB 3.0 CCD camera 206, such as may be obtained from Ximea GmbH of Minster, Germany, is also integrated into the handheld probe for concurrent acquisition of surface video images and mosaicking in real-time. Light for surface illumination is provided by a light-emitting diode coupled to an integrated fiber bundle. Light exits the distal fiber ends that are located in the nose cone of the probe. For acquisition of cross-sectional images, samples are manually scanned using the probe, and images are constructed based on the decorrelation of sequentially acquired A-scans, in accordance with teachings of Ahmad 2009. In an exemplary embodiment of the invention, the incident optical power was approximately 1.3 mW, which is well below the ANSI Maximum Permissible Exposure (MPE) limit for skin.

In the reference arm, a variable neutral density filter may be placed before the lens (f=60 mm) to optimize system sensitivity. The light reflected from both arms is recombined in the 2×2 fiber coupler, and the resulting spectral interference signal is captured by the OCT spectrometer 208. Spectral data from the line scan CCD camera of the spectrometer is coupled to at least one processor adapted to operate as described below. In particular, data may be sampled and rescaled as a function of the wavenumber to display A-scans in real time.

In one exemplary embodiment, during image acquisition, the line rate of the CCD camera was set to 10 kHz and the camera exposure time was set to 200 µs.

Figure 3:
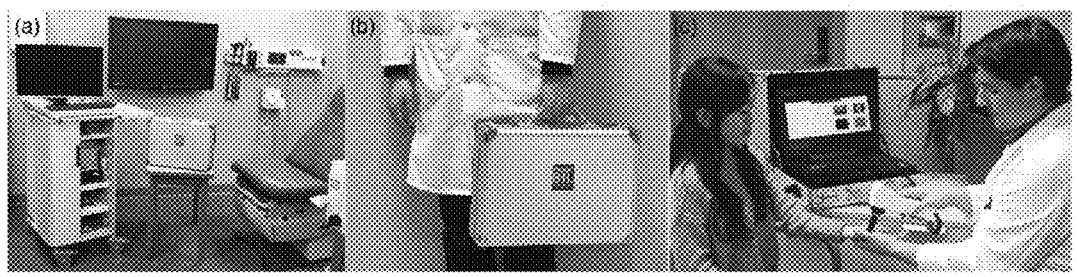
FIG. 3 shows a comparison of a compact briefcase OCT system in accordance with an embodiment of the invention with a conventional cart-based system.

FIG. 3 shows photographs of the portable briefcase OCT system (FIG. 3(b-c)) along with a prior art, cart-based low-coherence interferometry (LCI) system (FIG. 3(a)) described, for example, in Won et al., "Pneumatic low-coherence interferometry otoscope to quantify tympanic membrane mobility and middle ear pressure," Biomed. Opt. Express, vol. 9, pp. 397-409 (2018). FIG. 3(b-c) shows the portability of the briefcase OCT system where a user/physician can easily carry the system to the primary care and/or remote setting.

Exemplary System Characteristics

Figure 5:
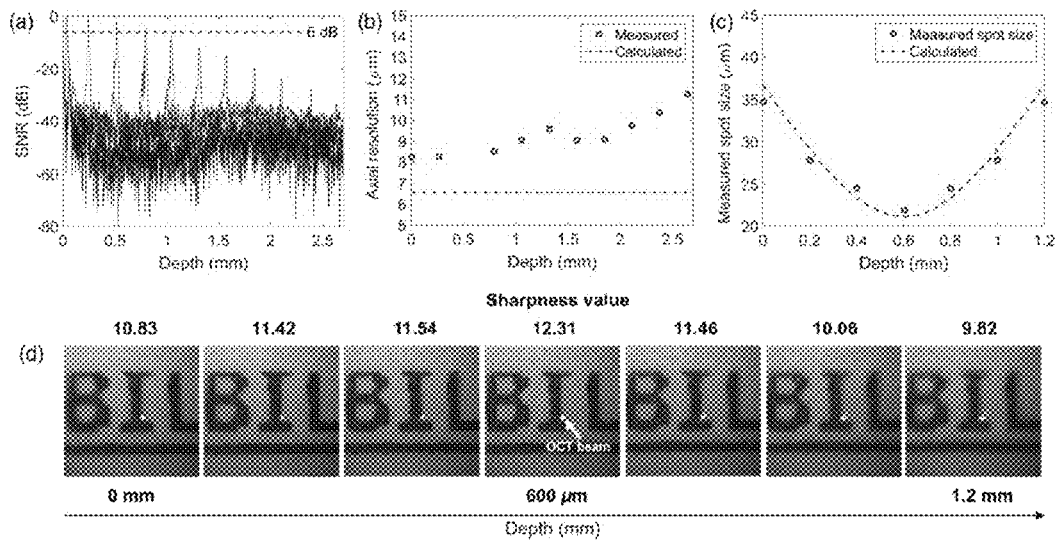
FIG. 5 is a characterization of a compact briefcase OCT system in accordance with an embodiment of the invention.

In one exemplary system, in accordance with an embodiment of the invention, the sensitivity of the system was measured by placing a mirror and an optical density filter (OD=2.1, round trip loss 42 dB) in the sample arm beam. FIG. 5(a) shows the measured sensitivity of the system to a depth of 2.7 mm in air. The measured sensitivity at zero optical path difference (OPD) was approximately 98.89 dB, and dropped by 6 dB at a depth of 1 mm in air. For in vivo imaging (shown below), a depth range of 1.5 mm (85 dB) was used, as the sensitivity was degraded over larger depths and was closer to the noise floor.

FIG. 5(b) shows the measured and calculated axial resolution of the system. The calculated axial resolution based on the SLD specifications from the vendor was around 6.2 am. The axial resolution was measured at the FWHM of the point spread function and was around 8.1 µm at zero OPD. The 2 am discrepancy in axial resolution may be due to slight uncertainty in dispersion correction. The measured axial resolution deteriorates with larger imaging depths (over 2 mm) Nonetheless, for an imaging range up to 1.5 mm, the system had minimal degradation compared to the zero OPD. FIG. 5(c) shows the measured and calculated lateral resolution of the system. The calculated lateral resolution was based on the focal length of the objective f=60 mm) and the measured beam diameter before the objective (3 mm), and was around 21.4 am. For imaging, we placed the focus roughly at 600 am depth. The Gaussian beam spot size (lateral resolution) was measured using a beam profiler (Thorlabs, BP209-VIS), as depicted. FIG. 5(d) shows the representative surface images and sharpness values for the corresponding depths and lateral resolutions shown in FIG. 5(c). At focus, the image demonstrated a maximum sharpness value (x) which decreases away from focus.

Cross-Sectional Imaging Using a Motorized Translation Stage

To demonstrate cross-sectional imaging using the briefcase OCT system, an image of layered tape was obtained by translating the sample using a motorized translation stage. FIG. 6(a) shows a cross-sectional image of the layered tape wherein more than 15 layers are clearly visualized. The dimensions of the acquired B-mode image was 7 mm×1.5 mm, with 512 axial points in depth along each A-scan, and with 1000 A-scans of data making up the cross-sectional B-mode image. The image of the layered tape shows that the current imaging resolution and depth are sufficient for imaging biological samples.

Figure 6:
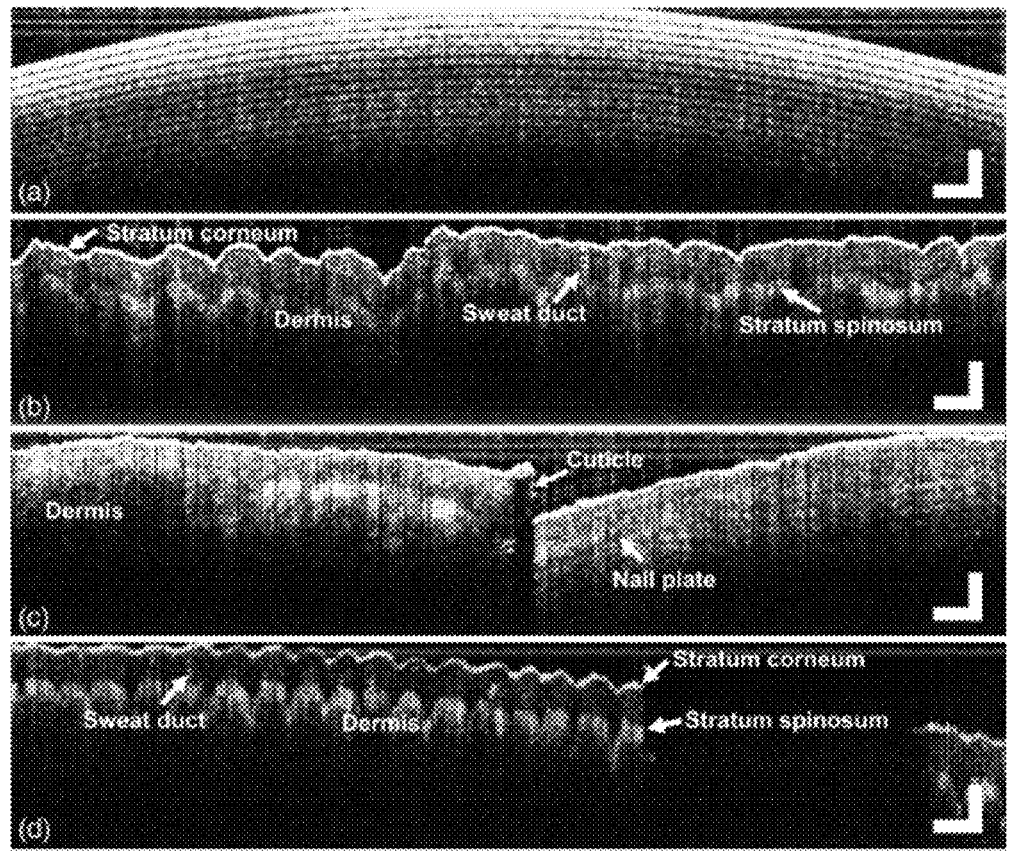
FIG. 6 depicts cross-sectional images obtained by a compact briefcase OCT system in accordance with an embodiment of the invention.

Human skin sites including the palm region, nail fold, and fingertip were also imaged. The dimensions of the acquired B-mode images were the same as for the layered tape. FIGS. 6(b-d) show representative cross-sectional images of these sites. Our system was able to resolve intricate features in the palm and fingertip such as the stratum corneum, stratum spinosum, sweat ducts, and the dermis layer. The image of the nail fold revealed features such as the epidermis, dermis, and nail plate. Acquisition of B-mode images using a motorized stage was done to compare image quality with cross-sectional images assembled using the manual scanning approach.

Manual Scanning. Mosaicking and Cross-Sectional Imaging Approach

Figure 7:
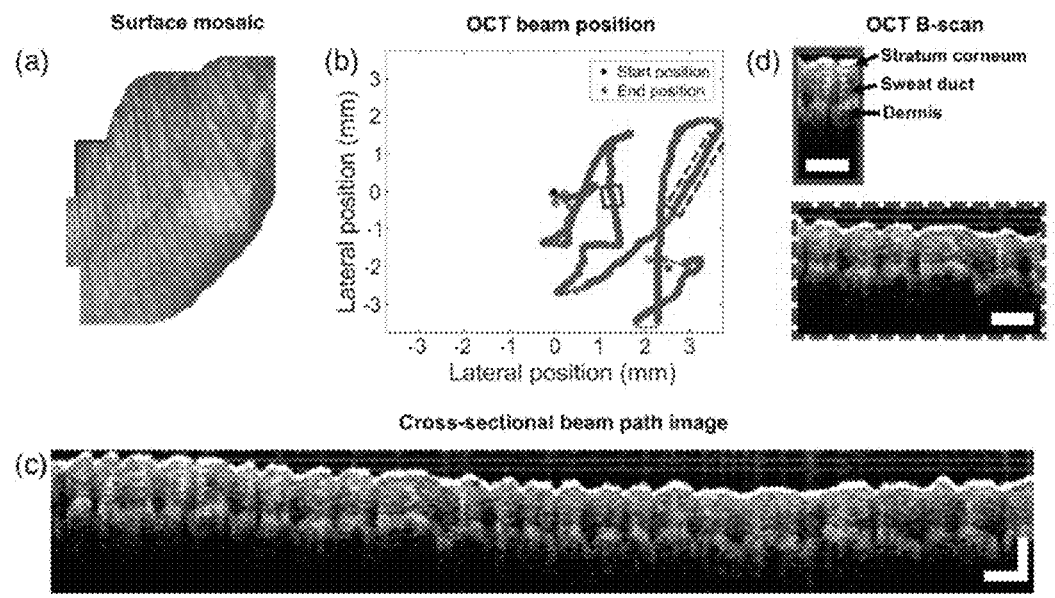
FIG. 7 is a cross-sectional beam path image and surface mosaic of an in vivo human palm acquired by a compact briefcase OCT system in accordance with an embodiment of the invention.

Implementation of manual scanning and real-time mosaicking is now described with reference to imaging in vivo human skin. FIG. 7 shows the OCT and surface image mosaic of skin from the human palm. The real-time surface mosaicking shows precise image registration, resolving the papillary ridges (fingerprint) of the skin in the palm region (FIG. 7(a)). FIG. 7(b) represents the plot of the OCT beam position during the real-time scan. This position plot is based on the measured offset value of the image registration corresponding to the acquired A-scan position. The cross-sectional beam path image generated for the integrated path of the OCT beam position is shown in FIG. 7(c). The represented image shows well differentiated structures such as the stratum corneum, sweat ducts, and the dermis. This image has a lateral dimension of over 10 mm and was obtained from both dimensions (X and Y) in the beam path position. The system and method described herein allows a user to manually and arbitrarily scan larger FOVs. Furthermore, the recorded path of the beam position enables the construction of a thickness map that could be overlaid on the surface image mosaic. FIG. 7(d) shows representative B-scans obtained from the same dataset at two different straight paths highlighted in FIG. 7(b). The B-scans obtained from this manual scanning approach are comparable to the B-scans obtained using the motorized stage. The results from imaging the palm show that the system and method described herein can clearly resolve micro structural features in scattering samples.

Figure 8:
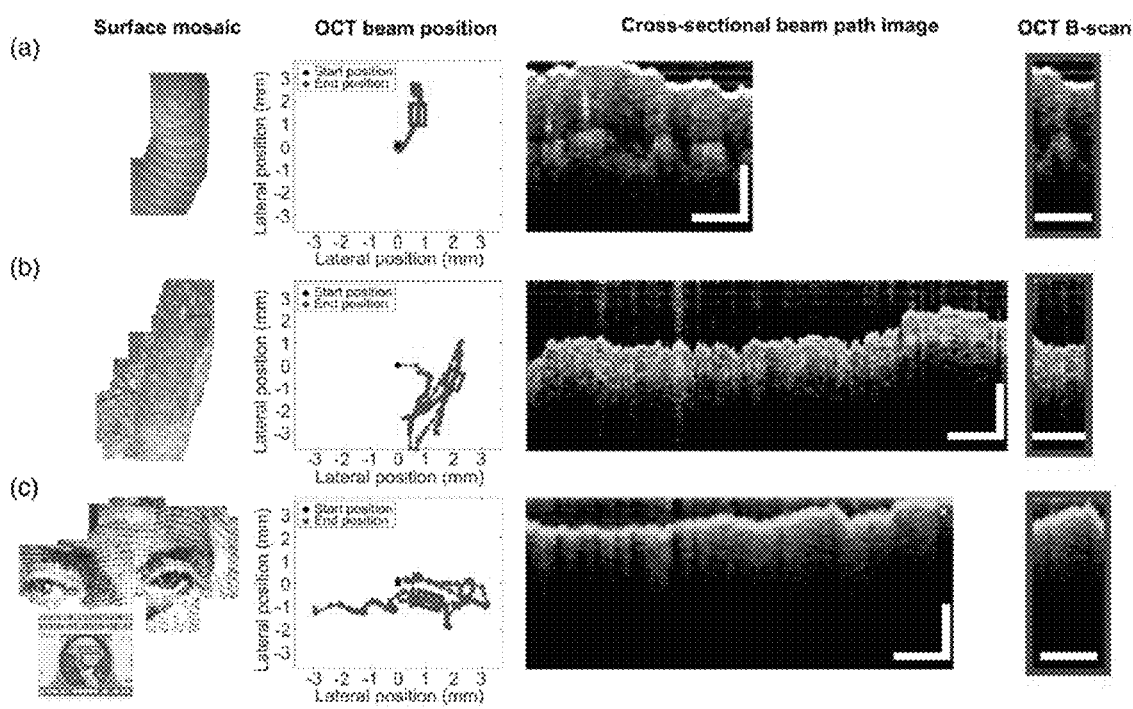
FIG. 8 depicts cross-sectional beam path images and surface mosaics of human skin tissue and a dollar bill acquired by a compact briefcase OCT system in accordance with an embodiment of the invention.

The human fingertip and forearm regions have also been imaged employing methods in accordance with the present invention. The OCT and surface image mosaics from both tissue sites resolved optimal surface features and depth-resolved structures (FIG. 8(a, b)). Cross-sectional images and the corresponding surface mosaic of paper currency are shown in FIG. 8(c). A dollar bill was imaged to highlight the accuracy of the image registration and the real-time mosaicking algorithm, as fine features can be resolved in the surface image mosaic. The cross-sectional image of the dollar bill, however, lacks structural features, and largely only a surface reflection could be visualized by OCT. From these results, it can be concluded that the briefcase OCT system with manual scanning and real-time mosaicking can accurately and simultaneously construct surface and depth-resolved cross-sectional images in real-time.

Real-Time Mosaicking and B-Scan Formation

Figure 4:
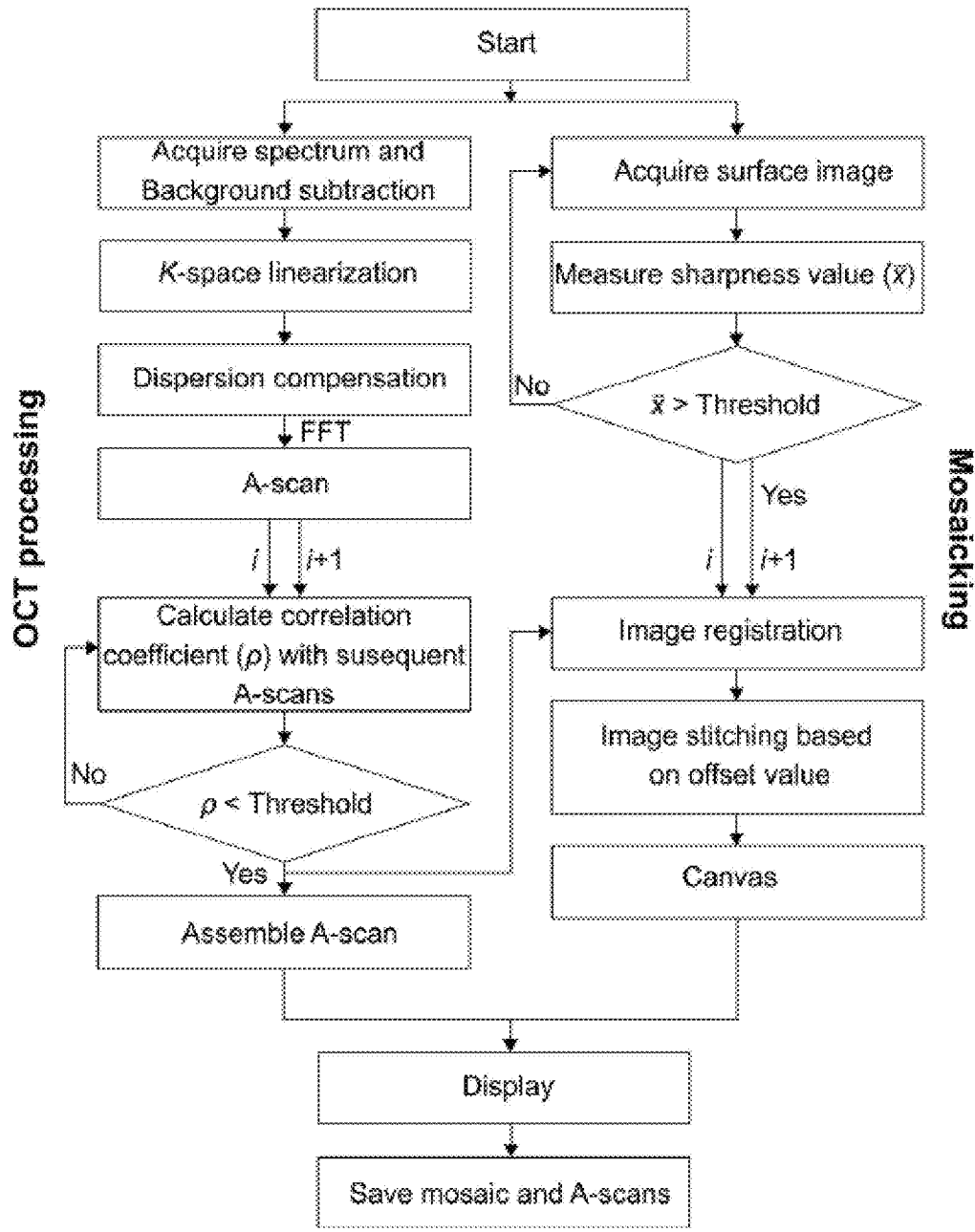
FIG. 4 is a flowchart showing real-time OCT acquisition and surface image mosaicking in accordance with an embodiment of the invention.

The algorithm used for OCT acquisition, image assembly, and surface image mosaicking is illustrated in the flowchart in FIG. 4. The processing may be performed using a custom-designed graphical user interface (LabVIEW 2015, available from National Instruments, Austin, Tex., USA) on a laptop computer. Initially, background spectra and resampling indices for linearization in wave number are pre-calculated in the initialization step. Standard OCT processing is then performed by background subtraction, cubic B-spline interpolation for linearization, and dispersion compensation. This is followed by A-scan reconstruction by taking the Fourier transform of the recorded spectral signal. Reconstruction of cross-sectional images is implemented with a manual scanning approach as described above. The use of this manual scanning method to generate cross-sectional images is implemented to minimize cost, to eliminate a lateral scanning mechanism, and to enable imaging over larger areas of tissues.

A-scan assembly is based on a defined cross-correlation threshold value set by the user, where the cross-correlation of two sequential A-scan (i and i+1, where i corresponds to the first A-scan) is computed. The A-scans are appended to the assembled images when the correlation coefficient falls below the threshold (implying that the new A-scan is from a new lateral location), and excluded from the assembled images when the correlation coefficient is greater than the threshold (implying that the new A-scan is from the same lateral location). The decorrelation of the A-scans effectively confirms displacement of the probe beam or a change in the sample structure, which otherwise would have a higher correlation coefficient. A threshold value for the correlation coefficient in the study disclosed herein was empirically set to 0.8 for image assembly.

The developed algorithm also simultaneously acquires surface images of the sample and performs mosaicking in real-time. For efficient data flow, a producer/consumer architecture in LabVIEW was implemented where the producer loop acquires surface images and the consumer loop does the mosaicking of acquired images in real-time. The consumer loop starts only when the correlation coefficient is below the threshold level and will be notified using a notifier (as shown in FIG. 4). The notifier also synchronizes the acquired A-scans for each surface image in the mosaic. This allows for the determination of the lateral 2D position of the OCT beam, and subsequently for more standard B-scan images to be extracted from regions of straight paths identified from within the total path of the beam.

For real-time mosaicking, out-of-focus or blurred images are eliminated to form a high-quality mosaic. Blurry images could also result in an error in the registration algorithm. Our algorithm incorporates a command to eliminate out-of-focus images in real-time by measuring the sharpness of the image. The sharpness value (or mean value, x) of the image is measured by taking the mean of the convoluted image using a linear filter, which effectively highlights the features of the image. For real-time processing, the threshold value may be set to correspond to the sharpness value at a depth of 0 mm and 1.5 mm (FIG. 5(d)), and any images acquired outside of these depths are excluded.

The surface image registration algorithm determines the translational offset between two consecutively acquired frames. A fast registration algorithm was implemented, since this approach requires a small fraction of computational time and memory requirement. The fast registration algorithm performs a cross-correlation using the discrete Fourier transform between consecutive images. The registered images are subsequently inserted into a predefined zero matrix (also called a canvas) where the first image is copied to the center of the canvas and subsequent frames are copied with an offset value. The stitching of images is based on the dead-leaf approach where a new frame over-writes an existing frame. The canvas size is approximately 5 times larger (FOV: 15 mm×15 mm) than a singly-acquired frame, and the time required for image registration is approximately 10 ms. The program saves the surface image mosaics as 12-bit PNG images, and the assembled A-scans both as raw data and as a 12-bit PNG image.

It is to be noted that generating cross-sectional images from the A-scans is only possible if the density of the A-scan measurements is high enough. In addition, the 2D positions of the A-scans need to be arranged linearly across the TM to generate cross-sectional images or B-scans. However, even if the A-scans are not linearly arranged or if they are sparsely or randomly distributed across the TM, the system and method described herein can still determine where they were acquired based on the surface images synchronized with the A-scans. Thickness maps can then be created for the locations on the TM where A-scans were acquired. Such thickness maps relay important information about the thickness of the TM and any biofilm or fluid behind it in the middle ear space. One way to calculate the thickness of the TM is to compute the axial thickness of the TM for each A-scan by finding the distance between the first and last peak at the position of the A-scan. Peak positions at $(x_m, y_{n,top})$ and $(x_m, y_{n,bottom})$, for example, would result in an axial thickness of $y_{n,top} - y_{n,bottom}$. However, any other method of determining the thickness of the TM known to person skilled in the art could be used to generate the thickness map, such as the radial thickness described below.

Assessment of Disease States of the Middle Ear

Machine learning (ML)-based assessment techniques have been demonstrated in the objective interpretation and classification of middle ear data obtained via OCT techniques as described above. ML approaches are currently in development to supplement radiologist and pathologist capabilities for most medical imaging techniques (X-ray, CT, MRI, Hematoxylin and Eosin-stained pathology, and ultrasound imaging), following existing standardized diagnostic criteria. Some of these approaches are even beginning to exceed the average radiologist performance. Guidelines for the identification and classification of disease states with OCT imaging are currently under development for ophthalmology, cardiology, intravascular imaging, dermatology, and other applications, although none exist for otolaryngology applications or OM.

In the description to follow, existing clinical standards are used to define diagnostically relevant parameters of OM infection, including morphological, optical, and clinical features of OM infection states commonly encountered by both primary care physicians and otolaryngologists. A comprehensive framework has been designed to extract features, classify data, and present clinically relevant results in an easy to use package. Metrics derived from 58 independent subject datasets, including 58 OCT B-mode images, 52 digital otoscopy images, and 54 physician's reports, were used in this study. After feature extraction, a database consisting of 25,479 entries was generated for training and testing the classifier. Each extracted OCT A-line was treated as a single data point, with 20 columns corresponding to the different features for each A-line. The features are extracted from OCT data (12 features), otoscopy images (6 features), and information available to the physician at the time of exam (2 features). While each OCT-feature is unique to each extracted A-line, the features obtained from clinical data (i.e., otoscopy images and physician reports) were duplicated to correspond to each subject. If any component of the dataset was not available, the entries for that specific metric (otoscopy image or report) were left empty.

An automated ML-based platform, referred to herein as a classifier, classified this dataset to discriminate A-line scans from normal, healthy ears ($N_{entries}$=8,572, $N_{subjects}$=17), from those with middle ear biofilms ($N_{entries}$=3,748, $N_{subjects}$=9), and middle ear biofilms and fluid ($N_{entries}$=13, 159, $N_{subject}$=32). These three initial groupings help to identify pathological conditions which could require pharmacological or surgical intervention for treatment. Class labels or "ground truths" for training data were based on two different metrics: using the analysis of the OCT B-scans in a small reader study by three experts familiar with OCT imaging and OM, and by the physician's final diagnosis contained in the report. Of the 20 features used for classification, different subsets can be selected and compared to observe the performance of features related to OCT data against what is available to the physician through otoscopy, and eventually the performance of the most useful features for classification. Similarly, 23 different classifiers were used to analyze this data. Representative results obtained from a custom-designed random forest classifier were tested with both ground truths and compared against other standard classifier types (support vector machine (SVM), K-nearest neighbor (KNN), and ensemble techniques) to ensure consistent performance.

The following description details results from the development and validation of this automated comprehensive framework, as well as the exploration of the predictive power of various feature subsets to identify OM in OCT images. Challenges for clinical translation and avenues for platform improvements are discussed. Finally, guidelines for minimum performance are explored, specifically for signal-to-noise ratio (SNR) and resolution, to adapt this method to any OCT system of sufficient performance and quality.

OCT System and Human Subject Imaging

A handheld OCT system was used to image human subjects and characterize various presentations of OM in past clinical studies. This system was comprised of a spectral-domain OCT system and handheld probe, with a center wavelength of 860 nm and an approximate bandwidth of 135 nm at FWHM. The system has an axial resolution of 2.4 μm and a lateral resolution of 15 μm. The system emits an optical power of 2.5 mW onto the tissue, which is well below the ANSI standard safety limits for incident exposure. A digital otoscope (Welch Allyn, USA) was used to collect acquire digital otoscopy images of the TM.

For an exemplary study described herein, 58 previously imaged subject datasets from pediatric subjects were selected from an internal data repository. Each dataset consists of a representative cross-sectional OCT B-scan image, a color digital otoscopy image, and a de-identified patient report, if available. These subjects capture the range of patient presentation of OM, consisting of healthy normal controls, and subjects diagnosed with a range of OM infection states: acute otitis media (AOM), otitis media with effusion (OME), chronic otitis media with effusion (COME) and recurrent acute otitis media (RAOM). Clinical findings from each dataset are shown in Table 1, including the clinical impression of the presence of fluid as determined by a physician's assessment using otoscopy (OTO), and a reader examining OCT data (OCT). Discrepancies in the presence of middle ear fluid (MEF) between these two analysis methods are bolded.

TABLE 1

Clinical findings and consensus labels for OCT.

| # | Clinical Findings | OTO | OCT | Group |
|---|---|---|---|---|
| 1 | Bilat. ETD, mucoid COME | Y | Y | 2 |
| 2 | Bilat. ETD, mucoid COME | Y | Y | 2 |
| 3 | ETD, RAOM | Y | Y | 2 |
| 4 | Bilat. ETD and COME | Y | Y | 3 |
| 5 | No dictation avail. | — | Y | 3 |
| 6 | No dictation avail. | — | Y | 3 |
| 7 | No dictation avail. | — | Y | 3 |
| 8 | No dictation avail. | — | Y | 3 |
| 9 | Bilat. ETD, mucoid COME, HL | Y | Y | 2 |
| 10 | Bilat. ETD, COME | Y | Y | 3 |
| 11 | Bilat. ETD, COME | Y | Y | 2 |
| 12 | Bilat. ETD, COME | Y | Y | 2 |
| 13 | ETD, RAOM | Y | Y | 3 |
| 14 | ETD, RAOM | Y | Y | 3 |
| 15 | RAOM with effusion | Y | Y | 3 |
| 16 | Bilat. COME, RAOM, ETD, HL | Y | Y | 3 |
| 17 | RAOM, hearing loss | Y | Y | 2 |
| 18 | RAOM, hearing loss | Y | Y | 2 |
| 19 | Bilat. ETD, COME | Y | Y | 3 |
| 20 | Bilat. ETD, COME | Y | Y | 3 |
| 21 | Bilat. ETD, COME | Y | Y | 3 |
| 22 | Bilat. ETD, COME | Y | Y | 3 |
| 23 | Bilat. ETD, COME | Y | Y | 3 |
| 24 | ETD, RAOM | Y | Y | 3 |
| 25 | Bilat. ETD, COME | Y | N | 1 |
| 26 | Bilat. ETD, COME, HL | Y | Y | 3 |
| 27 | Bilat. ETD, COME | Y | N | 1 |
| 28 | Acute URI (persistent cough) | N | N | 1 |
| 29 | Normal control | N | N | 1 |
| 30 | Normal control | N | N | 1 |
| 31 | Normal control | N | N | 1 |
| 32 | Normal control | N | N | 1 |
| 33 | Normal control | N | N | 1 |
| 34 | Normal control | N | N | 1 |
| 35 | Normal control | N | N | 1 |
| 36 | Normal control | N | N | 1 |
| 37 | Bilat. OME | Y | Y | 3 |
| 38 | Bilat. OME | Y | Y | 3 |
| 39 | Bilat. OME | Y | Y | 3 |
| 40 | Dull TM | N | N | 2 |
| 41 | Normal control | N | N | 1 |
| 42 | Bilat. AOM | Y | Y | 3 |
| 43 | Bilat. AOM | Y | Y | 3 |
| 44 | RAOM | Y | Y | 3 |
| 45 | Normal control | N | N | 1 |
| 46 | Normal control | N | Y | 3 |
| 47 | No OM complaints | N | Y | 3 |
| 48 | OME | Y | Y | 3 |
| 49 | Opaque TM | Y | Y | 3 |
| 50 | No OM complaints | N | Y | 3 |
| 51 | No dictation avail. | — | Y | 3 |
| 52 | Normal control | N | N | 1 |
| 53 | OME | Y | Y | 3 |
| 54 | Dull TM, OME | Y | Y | 3 |
| 55 | AOM | Y | Y | 3 |
| 56 | Normal control | N | N | 1 |
| 57 | Normal control | N | N | 1 |
| 58 | Normal control | N | N | 1 |

OTO: Fluid identified by the physician using otoscopy, and OCT: fluid identified using OCT data. Discrepancies in fluid identification are bolded. Group # set by OCT reader study. Bilat: Bilateral; ETD: Eustachian tube dysfunction; COME: Chronic otitis media with effusion, RAOM: Recurrent acute otitis media, HL: Hearing loss; URI: Upper respiratory infection; TM: tympanic membrane.

OCT Image Groupings and Reader Study

Figure 9:
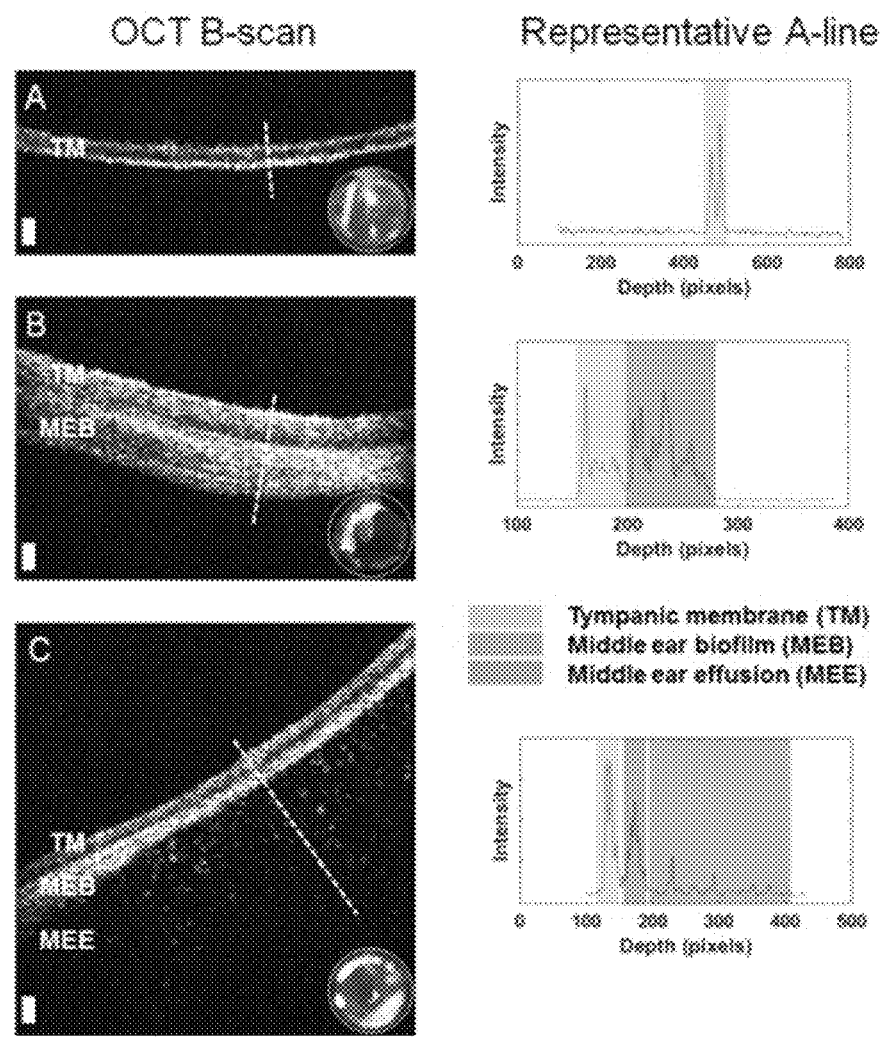
FIG. 9 shows representative OCT cross sectional images and A-line profiles acquired by a compact briefcase OCT system in accordance with an embodiment of the invention.

To interpret and label OCT training data appropriately, a small blinded reader study was performed. Three expert OCT readers familiar with OCT, OM, and middle ear imaging were trained through a guided analysis of sample images from each group consisting of data not included in this study. Then, the reader evaluated and classified each OCT image in this dataset into one of the group classifications used in this study ("Normal", "Biofilm", "Biofilm and Fluid"). Trends identified in OCT images were used to develop these groupings, as no currently accepted noninvasive clinical techniques provides information related to the presence of middle ear biofilms. These groupings were developed from our past observational clinical studies where OCT images of subjects with OM were correlated with a physician's clinical findings, or intraoperative OCT imaging was directly compared to surgical intervention and microscopy findings during TT surgery. Normal cases were identified by a TM of approximately 100 micrometers thick and the lack of any additional structures observed in other infection states. The second grouping ("Biofilm") was created as otoscopy does not provide an indication of the presence of a middle ear biofilm, perhaps only the appearance of a dull, thickened, or opaque TM. The third grouping ("Biofilm and Fluid") was created due to the presence of a biofilm in all scans that contained MEF. These classes are shown in FIG. 9. Further discussion of these correlative studies and results are described in the following publications, all of which are incorporated herein by reference:

Pande (2017).

Monroy et al, "Noninvasive in vivo optical coherence tomography tracking of chronic otitis media in pediatric subjects after surgical intervention," *Journal of Biomedical Optics*, vol. 22, 11, (2017).

Monroy et al., "Non-invasive optical assessment of viscosity of middle ear effusions in otitis media," *Journal of Biophotonics*, vol. 10, pp. 394-403, (2016).

Monroy et al, "Direct analysis of pathogenic structures affixed to the tympanic membrane during chronic otitis media," *Otolaryngology—Head and Neck Surgery*, (2018).

Pande (2016).

Zhao, Y. et al., "Rapid diagnosis and differentiation of microbial pathogens in otitis media with a combined Raman spectroscopy and low-coherence interferometry probe: Toward in vivo implementation," *Journal of Biomedical Optics* vol. 21, 107005, (2016).

Nguyen, et al, "Investigation of bacterial biofilm in the human middle ear using optical coherence tomography and acoustic measurements," *Hearing Research*, vol. 301, pp. 193-200, (2013).

Nguyen et al, "Noninvasive in vivo optical detection of biofilm in the human middle ear," *Proceedings of the National Academy of Sciences*, vol. 109, pp. 9529-35, (2012).

Nguyen et al, "Non-invasive optical interferometry for the assessment of biofilm growth in the middle ear," *Biomedical Optics Express*, vol. 1, pp. 1104-16, (2010).

The consensus or majority vote of the 3 readers was used as the final label for this classification. Overall, there was little variation in reader assessment. In 58/58 scans, at least 2/3 readers agreed on the group label, with all readers completely agreeing on 38/58 subjects.

The definition of classification criteria follows a framework of three major components: Extraction of Features from Data; Selection/testing of Ground Truth; and Display and Presentation of Data. These are now described.

Framework Element 1 of 3—Defining and Extracting Features from Data

Features were developed to extract or capture inherent qualities of tissue, utilizing a physical, structural, or optical metric to numerically quantify infection states. A broad range of statistics and metrics were chosen.

Features Derived from OCT Data

All OCT images are first median filtered using a 2×2 kernel and window averaged by a 5-pixel lateral window to reduce noise or speckle and increase uniformity for analysis. Next, the image area is automatically segmented, and a depth profile of each position is isolated, which is taken radially from the TM surface into the MEC.

One method to isolate the depth profile is described above in reference to the TM thickness map. However, since B-mode OCT images are available in this study, an alternate method was developed. Radial thickness takes advantage of information adjacent A-scans in an OCT B-scan to detect and calculate thickness through a point normal to the tissue surface. Each A-scan is run through the peak finding algorithm as described above to find the top edge of the tissue using the first peak, where a point is added to a mask image in the same location if it is within a separation window. As each A-scan is processed, a point-cloud like mask is generated for the top line. As this algorithm traverses each A-scan, each point must be within a fixed separation window from the previously identified point: $(x_m, y_n) \rightarrow (x_{m+1}, y_{n+1})$, $\Delta y <$ Separation Window.

The surface of the TM is relatively flat when comparing adjacent pixels, even after window averaging, such that adjacent points that vary wildly are likely due to a misidentification in the peak finding algorithm. If no peak is detected, or a peak is detected outside the separation window, it is discarded and the separation window on the subsequent iteration dynamically increases until a new peak is found. This behavior prevents failure from occurring when processing slightly obscured regions of tissue, discontinuities in tissue surface, or in regions of low SNR which often occur during imaging if the ear canal or ear wax partially obscures the cross-sectional OCT beam. Once a point is eventually found on a subsequent iteration, the separation window is reset to its original value. Once the top point mask is generated, the mask is thresholded using the original intensity image to reduce the effect of outlier points, and a $4^{th}$ order polynomial is fitted to this line, which tries to find the average path through these points and is set aside as $y_t$op:

$$y_{top\backslash bottom} = Ax^4 + Bx^3 + Cx^2 + Dx + E$$

The bottom point mask and fitted curve is similarly created, instead using the last detected peak and using a separation window with a starting value 3 times greater than the top curve. This allows for proper detection if points in deeper areas of the image where sparse scatterers, detector roll-off, and low SNR play a larger role than near the zero-delay or top of the image in the OCT system. Functionally, this ensures areas of low-scattering fluid in OCT images are more likely to be detected.

Once these two polynomial curves are generated, the radial thickness of each A-scan is calculated by translating across each point on the top line, using these known point $(x_{1:m,\ top}, y_{1:n,\ top})$ to find a solution on the bottom curve. This occurs in one of two ways depending on the curvature local to each point. First, a normal line from the top curve is calculated:

$$m_{NormTop} = \left(\frac{\partial(y_{top})}{\partial x}\right)^{-1}$$

$$y_{NormTop} - y_{n,top} = m_{NormTop}(x - x_{m,top})$$

Then, intersection points with the bottom curve are identified, if possible:

$$\text{Solve} \rightarrow (x_{solution,bot}, y_{solution,bot}); y_{NormTop} - y_{bot} = 0$$

The radial thickness ensures that the thickness of this region of tissue is more accurately mapped:

$$\text{Radial Thickness} = \sqrt{(x_{m,top} - x_{solution,bot})^2 + (y_{n,top} - y_{solution,bot})^2}$$

Empirically, this has been found to be more accurate and have a lower standard deviation across the tissue than the axial thickness described above. If no solution exists at the current position along the top line, a second method is employed to find the closest point on the bottom line. Typically, this occurs when the point of analysis on the top line is near the edge of the imaging window, and a normal line from the top curve does not have sufficient space to intersect with the bottom curve. In this case, the shortest distance is found from the analysis point to the bottom curve:

$$dist = \sqrt{(x - x_m)^2 + (y_{bot} - y_n)^2}$$

$$\text{Solve} \rightarrow (x_{solution,bot}, y_{solution,bot}); \frac{\partial(dist)}{\partial x} = 0$$

The distance to the analysis point is then computed (see equation for radial thickness above) is and is compared against both the equivalent axial thickness value for this same position and the thickness value from the previous iteration, if it exists. The minimum of these three values is then selected. A final check analyzes slope of the top line. If it is near 0, this indicates the analysis point is near a peak or valley and ensures the axial thickness is used.

This second part of the fitting process prevents some A-lines, typically near the edge of the image, from fitting to image data that would stretch past the edge of known data, and instead locks to the corner point on the bottom line. However, this may lead to an improper characterization of thickness. While the function of the lines that define the segmented area could still be calculated past the image boundaries, the points in these regions are undefined and could lead to significant errors. Ignoring these edge points reduces the overall dataset size by 20% (from 25,479 to 20,327 entries overall) and does not change the measured thickness values significantly. However, loss of data in this limited database will detrimentally impact short-term future performance, especially considering the overall accuracy of this platform was not significantly improved from this change. Since the dataset in this study was limited, including as many data points is of immediate interest to ensure the flexibility and stability of the described system and method. With additional data added to the classifier database over time, edge case A-scans can eventually be safely removed without much loss of performance or accuracy.

Twelve features are then extracted from each OCT radial depth profile. These features aim to quantify information about the optical properties of the tissue, which are known to vary with the disease-state of the ear, as described below. First, a peak-finding algorithm is used to quantify the density and distribution of tissue based on the location and distribution of scatterers in each depth scan. When comparing infection groups, this information can help differentiate the physical dimension, amount, and type of tissue when comparing infection states with varying amounts of solid tissue, fluid, and biofilms. To avoid erroneous peaks, thresholds are set dynamically to ensure measurements are above the noise floor at a given depth.

1: Optical thickness: The optical thickness of the TM and any associated MEB and/or MEF has been shown to be statistically linked to infection state. MEF, bacterial components, or MEB are present across varying infection states that are not present in healthy controls.

2: Standard deviation of Peak-position location: The distribution of scatters in depth relates to the amount of tissue detected by the OCT system and the relative distribution in depth. In healthy ears, only a handful of peaks will be identified within a 100 micrometer range, whereas in cases with an effusion or biofilm present, this value will be larger.

3: Mean of peak width: Peak width statistics may refer to the size and distribution of the scatterers, as with OCT it has been observed that MEF typically becomes more purulent as an OM infection progresses. The mean peak width may correlate to the average physical size of scatterers in a scan.

4: Standard deviation of peak width: The standard deviation of peak width may correlate to the distribution of physical sizes of scatterers in a scan.

5: Mean peak prominence: Peak prominence statistics may relate to the optical composition and distribution of scatterers, as interfaces of larger differences in the local refractive index differences give rise to more intense OCT signals. During OM infection, the TM becomes inflamed with interstitial fluid and blood which have different optical properties to that of bacteria and mucous, and scatterers within any effusion. Mean peak prominence may correlate to the different optical properties of scatterers compared to the incident medium.

6: Standard deviation of peak prominence: The standard deviation of peak prominence correlates to the distribution of optical composition in a single scan.

7: Total number of peaks: The total number of peaks is expected to follow the density of tissue, and increase with the presence of any fluid or biofilm during infection. Scattering distributions or profiles of normal and abnormal cases have been detailed in the prior art, or similarly in FIG. 9.

8: Optical attenuation maximum: OCT provides depth-resolved quantitative structural and functional information. The optical attenuation can be calculated by utilizing a previously developed method that calculates the depth-wise attenuation coefficient at each pixel:

$$\mu[i] \approx \frac{I[i]}{2\Delta \sum_{i+1}^{\infty} I[i]}$$

where $\Delta$ is the (depth) pixel size, and $I[i]$ is the intensity value at any given depth location i. This formula was applied over the previously fitted region of interest identified using the radial fitting from feature #1 to ensure it is calculated over valid points. This method provides numerical discrimination of the different scattering properties of different tissue types. The maximum attenuation in a single depth scan may differ between infection groups, related to the properties of differential components in healthy ears and in cases of infection.

9: Optical attenuation, Mean value in depth: The mean attenuation differential between infection groups will differ based on the additional presence of MEF and biofilm components.

10: Attenuation sum over peak-detected depth: This value will provide a measure of the overall signal attenuation in the depth scan. Scans with additional biomass are expected to have higher attenuation than scans from a healthy subject.

11: Fourier width of central peak: Fourier analysis of OCT A-line data may provide information regarding periodic or structured features in tissue, represented numerically by analysis of each peak width and prominence. The width of the central peak may provide differential frequency-based information related to the optical properties or size of present structures, such as sparse scatterers within a fluid (high freq.) or large instances of biofilm and fluid (low freq.).

12: Central Fourier peak prominence: The prominence of different scans may correlate to the ratio of low and medium frequency terms in an image, related to the optical properties of tissue compared to the incident medium.

Features from Clinical Data

Physicians perform a physical exam on each patient to assess their overall state of infection. This includes at minimum viewing the ear with an otoscope to assess the TM for infection, and often including a comprehensive physical that reviews overall health.

13: Otoscopy graded score/OMGRADE: Otoscopy images were analyzed using the OMGRADE scale, which provides a numeric score for grading the state of infection of the middle ear based on features identified with otoscopy. This scale ranges from 0-6 to distinguish different pathological conditions. Briefly, Grade 0 is a transparent TM in normal position, Grade 1 shows an identifiable fluid level, Grade 2 is an opaque identifiable fluid level in the MEC, while Grade 3 is a completely opaque TM although in a normal position. Grade 4 is a completely opaque and bulging TM, Grade 5 is an opaque TM with bullous formations or a contourless TM with swollen patches of keratin. Grade 6 corresponds to the presence of a perforation in the TM, retraction pocket, or cholesteotoma with or without discharge.

14: Physician's report score: Physician's reports are vital to properly correlate image-based features with clinical symptoms. Available reports were parsed for keywords that provide some indication of a healthy control or instances of otitis media infection and related risk factors. Each keyword was given a numerical value and an overall score was tabulated for each subject. Cues related to normal healthy controls or from OM-unrelated visits to the physician were awarded 0 points, such as 'unremarkable ears' or 'clear TM'. Keywords assigned 1 point include 'inflammation', 'effusion', 'erythema', 'inflamed', 'smoke', 'family history of OM'. 2 points were awarded to keywords such as 'Antibiotics', 'referral', 'persistent', or 'purulent'. Higher scores typically relate to more advanced infections. While this metric is empirical and specific to the language used in these reports, the composite score represents the clinical findings of the physicians involved in this study, and by extension the inherent difficulty in diagnosing OM. Other risk factors, such as the time of year of the report, age of the subject, and audiological exams (if available), were considered in this scoring system, but ultimately not included due to the complexity in assigning a score to multi-factorial data.

Finally, six metrics from digital otoscopy were used to discriminate normal and abnormal tissue given different color profiles of the TM typically observed as part of the physical exam. Although these values are not directly reviewed by physicians, this is one method to quantify the exam process. Digital otoscopy images were collected using a digital otoscope tool which ensured consistent illumination and sensor performance between imaging sessions. Ear wax acts as a confounding factor, often leading to bright regions in the image unrelated to infection state and were manually segmented out. Images were then converted to HSL to separate, extract, and quantify color (hue) and saturation separately from illumination information.

15: Hue—average value across otoscopy image: The various values calculated from the Hue of the image relate to the color of overall redness, injection, or erythema from the surface of the TM. The average value of Hue across an otoscopy image relates to the average color shade across the image of the TM.

16: Hue—median value across otoscopy image: The median value of Hue may provide differential information from the average, especially in cases where the TM coloration is skewed (non-uniform) across the image.

17: Hue—median absolute distance across otoscopy image: The median absolute distance provides a measure of spread, statistical dispersion, or in essence the width of the distribution of color shades in a single image.

18: Saturation—average value across otoscopy image: The various values calculated from the Saturation of the image relate to the intensity of the color of overall redness, injection, or erythema from the surface of the TM. The average value of Saturation provides another measure of the intensity of color, which likely relates to infection state.

19: Saturation—median value across otoscopy image: The median value of Saturation provides another related measure of the uniformity of the intensity of color.

20: Saturation—median absolute distance across otoscopy image: The median absolute distance provides a measure of spread, statistical dispersion, or in essence the width of the distribution of the intensity of color in a single image.

With these twenty features defined, each extracted depth profile will have 20 quantitative values calculated and placed in the corresponding table entry.

Framework Element 2 of 3 Selection/Testing of Ground Truth, Feature Set, Classifier For each classification experiment, several major elements must be selected: the classification method, the feature subset used in the classifier, and the ground truths assigned to the features that distinguish the groups.

Classifier Method:

A broad range of methods exist to perform classification tasks. In this study, a random forest (RF) classifier, described by Breiman, "Random Forests," Machine Learning, vol. 45, pp. 5-32, (2001), which is incorporated herein by reference, was chosen as the main method to classify this dataset. Other classifiers as known to a person having skill in the art may also be employed within the scope of the present invention. The exemplary RF-based classifier can reduce error in unbalanced datasets where data may be limited, is not sensitive to incomplete data within a specific data vector, such as missing otoscopy images or physician's notes, and can even rank the most useful features for classification. The performance of the RF classifier was assessed by following a "leave-one dataset-out" cross-validation strategy. Briefly, this strategy works by splitting N total images into a training set (N−1 images) and setting aside one image for testing. Each image in the dataset is tested on the trained classifier, and the mean accuracy is calculated across all loops or "folds", which serves to estimate the expected future performance on untrained data. In addition, the 95% confidence interval was calculated to validate and demonstrate consistency in performance. Alternately, twenty-two additional classifiers within the classification learner app in MATLAB® (The MathWorks, Inc., Natick, Mass.) were utilized to classify the dataset, consisting of SVM, KNN, and ensemble techniques.

Feature Subsets:

Different feature subsets can be utilized to compare the predictive ability of information gained from different parts of the clinical examination. If certain features are chosen, the resultant classification performance can help determine which features are most relevant to identify signs of OM in OCT images. In the results section below, the ability of otoscopy and OCT to identify the presence of fluid in subjects is tested with this platform, among other comparisons of interest.

Ground Truth:

To begin, the data are sorted and labeled to accurately reflect the clinical indications of the subject and the corresponding OCT metrics. The absolute ground truth for diagnosing OM is invasive surgical evaluation of the middle ear contents of each subject. However, when considering typical examination methods, invasive surgical inspection is impractical to perform given limitations of time and resources in daily practice. For this study, the ground truth basis was either derived from the physician's impression using otoscopy as in the clinical reports (DOC), or from the consensus of 3 readers analyzing OCT images as previously described (OCT). Table 1 above shows the results of each to identify fluid and the eventual class groupings. Comparing different ground truths in this manner allows a direct comparison between the capability of the current "gold standard" and a new technique such as OCT.

Framework Element 3 of 3—Displaying and Presenting Data

The presentation of the results from this framework was developed to be as relevant for clinical applications as possible. Two viewing modes, "Reader View" and "Developer View" are currently implemented. The "Reader view" is the default output, which annotates the OCT image with the predicted class of each depth profile and allows for quick visual interpretation of classifier results. The class is color coded to assist in quick discrimination of infection state, with "Normal" cases in green, "Biofilm" in yellow, and "Fluid and biofilm" in red. The expected class of the image and expected accuracy are displayed, ranging from High (greater than 80%), Medium (greater than 50%), Low (greater than 20%), and error. In "Developer View", the exact numerical classification accuracy is shown, which compares the expected class to the provided group labels in the training set data. This mode is useful when modifying feature detection, segmentation, or adding new features, to ensure proper functionality and performance. In principle, the complexity of the display modality can be adjusted to suit any range of needs. For example, it could display simply an error/green/yellow/red light, indicating the severity of infection or need for referral, or to retake a scan.

Results

Figure 10:
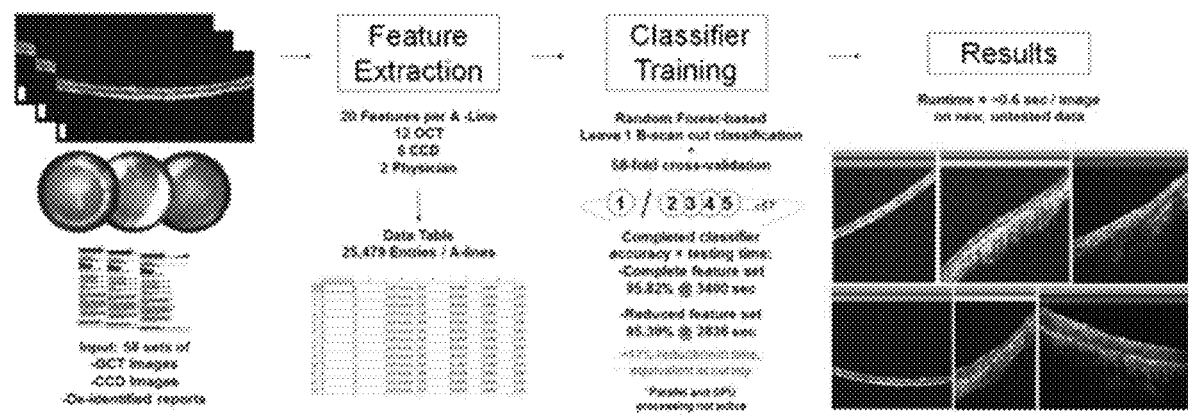
FIG. 10 shows an overview of a system and method in accordance with an embodiment of the invention.
Figure 11:
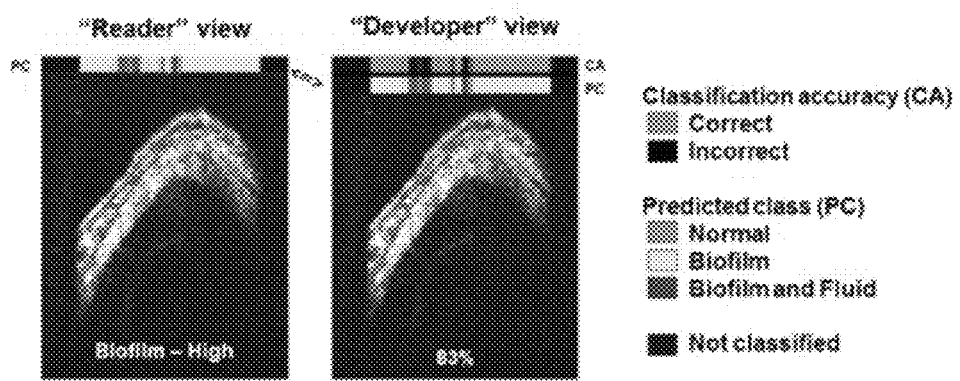
FIG. 11 depicts display modes for classified OCT images in accordance with an embodiment of the invention.

A breakdown of the overall platform operation is shown in FIG. 10. The automated platform first begins feature extraction on the database, which generates a large data table to be used for classification. Feature extraction for each subject's dataset required approximately 40 seconds. This table is then split into training and test groups to assess performance of the classifier using 58-fold leave one out cross-validation. Using all 20 available features for the training set, the RF classifier average classification accuracy was 95.82%, requiring only ~0.6 seconds per image for classification. Utilizing feature reduction strategies that ignore the worst 5 performing features (Least useful five removed, LU5R), accuracy remains relatively unchanged at 95.39%, yet the overall classifier training runtime is reduced by approximately 17%. Representative classified images from each group are shown in the rightmost panel of FIG. 10. FIG. 11 demonstrates the two display modes and annotations provided for each A-line when recombined into OCT B-mode images. Uncropped OCT images are shown in FIG. 11 in contrast to those in FIG. 9, demonstrating the limited preprocessing needed for data used in this platform.

Figure 12:
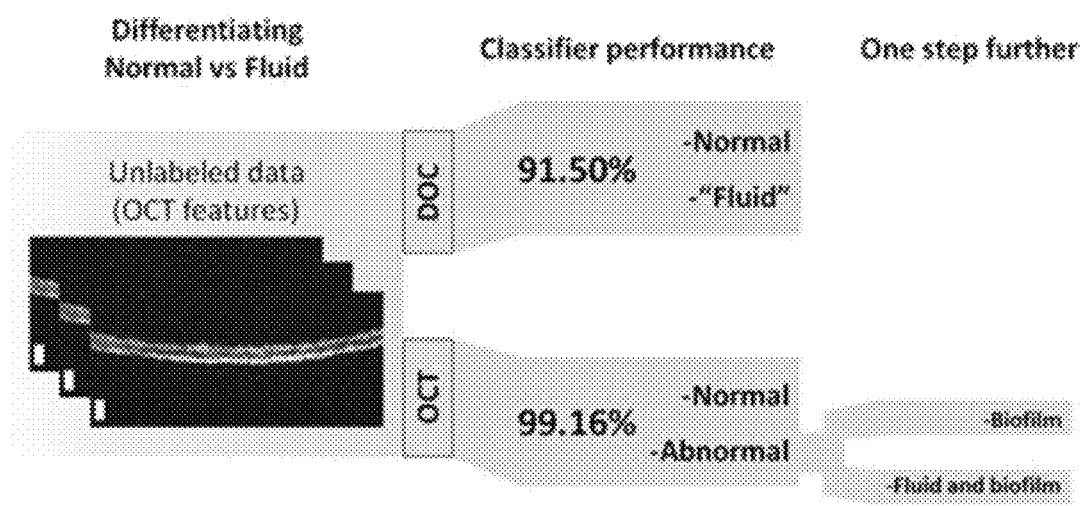
FIG. 12 shows a classifier output discriminating normal and fluid using OCT data in accordance with an embodiment of the invention.

With the development of the platform workflow and classifier pipeline, applied questions and challenges can be explored. To begin, a simple challenge was explored—can the platform detect MEF using OCT data as accurately as a clinician with otoscopy? An overview of this setup is shown in FIG. 12. The physician's diagnosis using otoscopy was used as the ground truth to identify symptoms of infection using OCT features, with an estimated future performance of 91.50% to distinguish normal and abnormal OCT scans with the physician (DOC) as the basis. These results show that the automated classification platform using OCT metrics to identify infection is equivalent to a physician's diagnosis with otoscopy 91.50% of the time. When using the same process, now with the ground truth derived from readers interpreting OCT data for abnormal scans, the predicted future performance increases to 99.16%. This result demonstrates that the platform can identify clinically indicated MEF in subjects as accurately as an expert human reader. Interpreting these results, the increased performance may be due to the improved capability of OCT to detect depth-resolved microstructural changes that point to infection, versus visual-only otoscopic observation, where signs of infection may be missed if subtle or unintentionally misinterpreted. Discrepancies between these two methods are bolded in Table 1.

These classification results alone represent a significant advancement for the diagnosis of OM using OCT, since accurately detecting signs of middle ear infection, including the presence of biofilms and fluid, is crucial to properly diagnose and subsequently treat any patient for OM. OCT may therefore be a noninvasive, effective, and unbiased tool to quantitatively detect signs of MEF and biofilms than otoscopy, especially without the need for an expert human reader with the addition of this automated analysis platform. Apart from identifying the clinical indications of fluid, further differentiation is possible between different types of abnormal scans based on depth-resolved OCT data, now between three groupings: "Normal", "middle ear biofilms", or "middle ear fluid and biofilms".

With this additional capability, additional questions and situations were then explored and compared using this dataset, such as: which metrics are the best predictors for middle ear infection or how do otoscopy metrics compare to OCT performance, with results detailed in Table 2. By isolating different clinical and OCT features for analysis, the utility of data from different sources (OCT or physician data) can be directly compared in identifying the likelihood of infection in subject datasets.

TABLE 2

Performance (accuracy) comparison results between a custom-designed RF classifier in conjunction with 22 other classifiers available in MATLAB ®, testing 8 feature subsets. 95% confidence interval provided for the RF classifier. Subset 7 shows 95.82% accuracy when discriminating normal, biofilm, and biofilm and fluid groups. Subset 8 reduces computation time by 17% and retains equivalent performance to subset 7. Worst performing ML-based classifiers shown below.

| | 1 | 2 | 3 | 4 | 5 | 6 | 7 | 8 |
|---|---|---|---|---|---|---|---|---|
| 95% CI+ | 70.72 | 55.27 | 70.72 | 86.04 | 87.72 | 82.66 | 96.04 | 96.54 |
| Random Forest (Custom) | 68.97 | 53.45 | 68.97 | 84.48 | 86.21 | 81.29 | 95.82 | 95.39 |
| 95% CI− | 67.21 | 51.62 | 67.21 | 82.93 | 84.69 | 79.92 | 94.7 | 94.23 |
| Ensemble (ML) | 74.60 | 74.70 | 56.00 | 74.50 | 81.60 | 78.70 | 88.90 | 90.00 |
| Type | SD | SD | SD | SD | SD | SD | SD | SD |
| SVM (ML) | 75.70 | 78.30 | 61.80 | 85.80 | 90.30 | 83.50 | 94.50 | 94.80 |
| Type | CG | CG | L | CG | L | L | CG | CG |
| kNN (ML) | 74.90 | 77.30 | 80.10 | 91.70 | 100.00 | 86.40 | 97.40 | 98.40 |
| Type | C* | C* | C* | C* | C* | C* | C | C |

C: Coarse; CG: Coarse gradient; L: Linear; ML: MATLAB ®; SD: Subspace Discriminant.
*all classifier subtypes had the same performance
Feature subsets
1 Clinical report keywords
2 OMgrade scale
3 6 Digital otoscopy metrics (custom)
4 Physician info (1 + 2)
5 All Clinical information (1 + 2 + 3)
6 12 OCT metrics
7 All 20 features (5 + 6)
8 Least useful 5 removed Feature subsets shown in Table 2 show how different pieces of information can be used to identify signs of infection in data. Using the RF classifier, subsets 1 (Clinical reports) and 2 (OMgrade scale—otoscopy) show that a single piece of information cannot efficiently be used to make a reliable diagnosis. This also demonstrates difficulties when using a single feature for classification. Clinicians do not necessarily have access to the custom created digital otoscopy metrics, such as in subset 3, although they are perhaps tangentially visually interpreted. These 6 metrics alone cannot accurately identify signs of infection either. When all clinical information is considered together (subset 4 or 5), reasonable performance is achieved.

Overall, classifier performance using data from the portable OCT imaging system is improved over subsets 1-3, in part due to the availability of more than a single feature available for classification. The 12 metrics extracted from OCT data (subset 6) perform well and are shown to be roughly equivalent to the performance of combined clinical information (~80%+). When all features are used together (subset 7) optimal performance is found at 95.82%. Subset 8 reduces the feature set by removing the worst performing features as determined by subset 7, which reduces computation time by 17% while maintaining equivalent performance (95.39%, −0.43).

Results from the classifiers within the MATLAB® Classification learner app are presented in Table 2. Results show that performance is relatively consistent across these different classifier types, tracking with feature subset, which indicates appropriate feature development and measurable differences inherent in the class groupings. At worst, subset 8 performance is at 90.00%.

Other tools may improve the diagnostic process for OM, and their incorporation within the scheme described herein lies within the scope of the present invention. MEF can be detected through several means, including gold-standard pneumatic otoscopy, ultrasound, and a recently developed short-wave infrared otoscope. The position of the TM can similarly be detected using light-field imaging. However, knowledge of the presence of fluid or position of the TM is not sufficient to diagnose OM. OCT imaging can provide one versatile solution to identify MEF and biofilms, and does not share many of the limitations of the aforementioned techniques. By providing simultaneous high-resolution, depth-resolved, and quantitative structural, functional, and optical characterization of tissue and MEF, OCT imaging can be performed non-invasively on awake subjects without any preparation of the subject or tissue for imaging.

The use of ML analysis to classify OCT imaging data of subjects with OM can provide a means to automatically classify data and provide a probable diagnostic outcome. It is to be understood that, while the application of machine learning to OCT imaging data is described herein in specific terms by way of example, all modalities of machine learning, to include deep learning and neural networks, may be employed for appropriate datasets, and are considered to lie within the scope of the present invention If an image is successfully collected, ML platforms could ensure the user would have a minimum baseline skill for detecting diagnostic markers for OM. This tool is intended supplement the assessment of the numerous quantitative details within data and apparent in tissue and integrate statistical measures to help guide decision making. In turn, with an accurate diagnosis, it may then be possible to provide the most appropriate and effective treatment for the current state of infection. In this sense, antibiotics could be properly prescribed when most effective, especially if no biofilm is present. Or, if a biofilm is identified with a lengthy infection history, evidence-based referral to a specialist could be possible. Finally, there may be other indications that an infection will clear and do not require treatment, which would require significant exploration and verification. This tool is not intended to replace critical thinking or clinical expertise, and, in its current form, is only a research tool and not a validated diagnostic device. However, with future testing and validation on a larger subject pool, this platform may allow for any non-expert user unfamiliar with OM and OCT to pick up this tool, collect a scan of the ear, and receive a probable clinical assessment or recommended course of action, such as referral to a physician or specialist for evaluation. In summary, tools such as these provide a baseline skill to users for a specific task and encourage evidence-based referral and treatment.

The classifiers in the MATLAB® software are designed to utilize, at minimum, a 5-fold cross-validation and the entire dataset to train the classifier. As a result of this built-in limitation, the accuracy results are considered to be overly optimistic in regards to future performance on untrained data. This is in contrast to the custom-designed RF classifier, which used a "Leave one subject-out" strategy, with K=N=58-fold cross-validation. The classifier is discarded after each training iteration rather than continuously retrained on all data, and recreated for the next iteration. This strategy attempts to more accurately simulate expected future use and performance of this platform, where an untrained and unknown dataset will be investigated using the classifier. This may explain why the kNN and other MATLAB® classifiers occasionally outperform the custom RF classifier. Different feature sets were also used to test the performance of features extracted from OCT data and clinical data. The best performance is found when a combination of features are used, indicating that both OCT and currently utilized clinical information together provide advantageous and necessary classification information.

Within the scope of the present invention, additional features may be added to the platform described herein to improve its versatility and robustness. For instance, data collection can be improved to allow for the calculation of the viscosity of any characterization of the detected scattering properties of in vivo MEF with OCT, which may allow for further discrimination of serous and mucoid fluid. To ensure usability for real-time analysis, algorithms that ensure rejection of unintended or unwanted imaging artifacts and reflections can be implemented, along with a notification system to kindly request the user to retake the data. Existing metrics and features can also be improved, such as expanding digital otoscopy analysis to include other metrics related to TM coloration, transparency, or opacity. The presentation of data may also be scaled to suit the expected use. In clinics with technicians or situations where a simpler screening or evaluation is needed, perhaps a simple binary output for 'normal' or 'recommend for clinical evaluation' can be assigned, along with a 'retake data' notification. In a more traditional clinical setting, some physicians may desire to see an expanded set of relevant information, which can be set to include metrics described above and full image data as needed.

Several points surrounding the present invention merit further discussion and clarification. The three class output labels that were used in this platform take into consideration immediately useful clinical information. In the future, many more infection states of OM and diseases or conditions of the TM can be added, such as TM perforations, dimeric TMs from previous surgical interventions, cholesteatoma, or myringo-/tympanosclerosis. This platform can easily expand to accommodate these additional states, although additional testing with appropriate and sufficient training data for each newly added condition will be required to assess accuracy. While OCT imaging can identify biofilms, there is no clinically accepted diagnostic method to noninvasively identify biofilms in the middle ear or any recommended course of action for treatment of a biofilm within current guidelines. Since biofilm-related infections are persistent due to their innate ability to resist antibiotic treatment and host immune response, it is expected that management strategies for chronic OM will follow treatment strategies used for other biofilm-mediated infections, such as cystic fibrosis or other respiratory infections.

The comprehensive framework described above in accordance with embodiments of the present invention was developed to allow for flexible testing and validation of the automatic identification of signs and symptoms of OM infection in OCT images. This platform was demonstrated and shown to have a predicted future accuracy of 95.39% using feature subset 8 (LU5R). With further development and testing of this platform, this framework could one day assist any untrained user to collect OCT data and receive a prediction for the presence of MEF and/or MEB—diagnostically relevant information for the current management of OM. More broadly, this platform may enable a true diagnostic and management platform for ear disease using OCT data.

Figure 13:
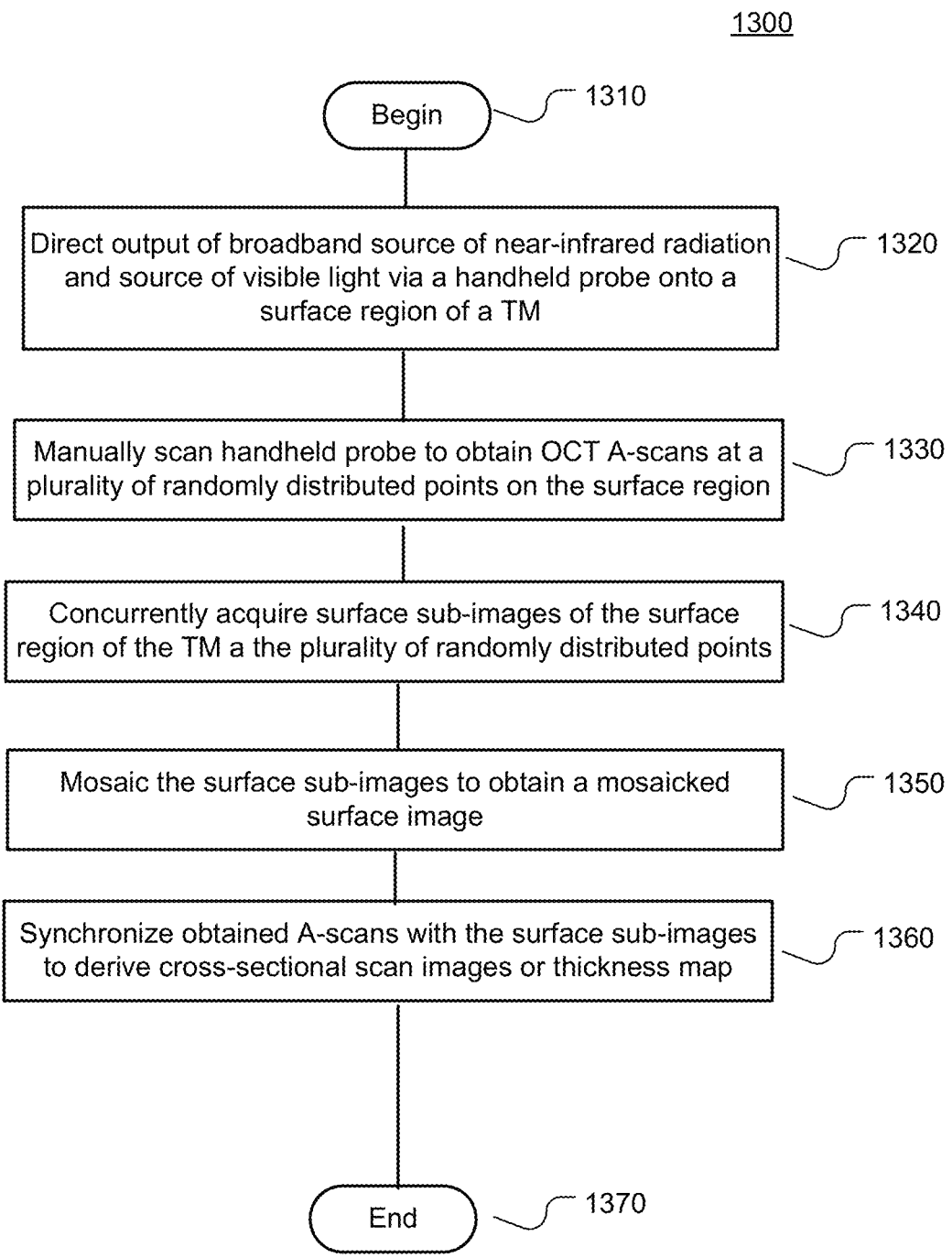
FIG. 13 is a flowchart of a method in accordance with an embodiment of the invention.

FIG. 13 shows a method 1300 in accordance with an embodiment of the present invention. The method begins at step 1310 and then proceeds to step 1320 where the output of a broadband source of near-infrared radiation and a source of visible light is directed onto a surface region of a TM via a handheld probe as described above.

In step 1330, the handheld probe is manually scanned to obtain OCT A-scans at a plurality of randomly distributed points on the surface region of the TM, as described above.

The method then proceeds to step 1340, where surface sub-images are concurrently acquired at the plurality of randomly distributed points on the surface region. The surface sub-images are acquired with a visible light camera in the handheld probe, as described above.

In step 1350, the surface sub-images are mosaicked to obtain a mosaicked surface image. An exemplary method to mosaic the surface sub-images is described above.

The method then proceeds to step 1360, where the obtained A-scans are synchronized with the surface sub-images. The synchronization may be performed by making use of the mosaicked surface image, as described above. Synchronization of the A-scans with the surface sub-images allows for determining the location of the A-scans within the surface region. The located A-scans can then be used to derive cross-sectional scan images (B-scans) of a volume behind the TM, as described above. The A-scans can also be used to derive a thickness map of the TM. The method ends at step 1370.

Figure 14:
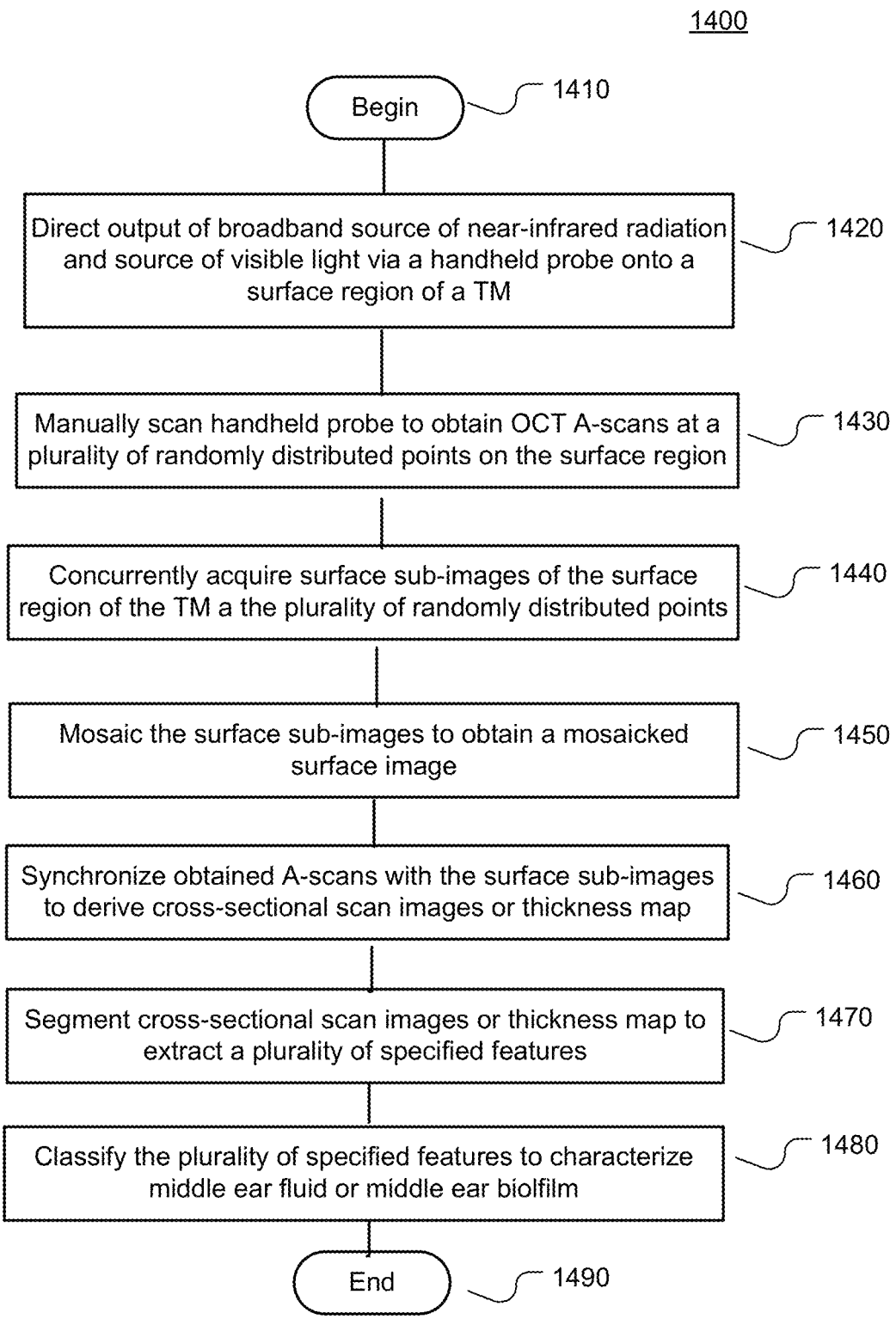
FIG. 14 is a flowchart of a method in accordance with an alternative embodiment of the invention.

FIG. 14 shows a method 1400 in accordance with an alternative embodiment of the present invention. The method begins at step 1410 and then proceeds to step 1420 where the output of a broadband source of near-infrared radiation and a source of visible light is directed onto a surface region of a TM via a handheld probe as described above.

In step 1430, the handheld probe is manually scanned to obtain OCT A-scans at a plurality of randomly distributed points on the surface region of the TM, as described above.

The method then proceeds to step 1440, where surface sub-images are concurrently acquired at the plurality of randomly distributed points on the surface region. The surface sub-images are acquired with a visible light camera in the handheld probe, as described above.

In step 1450, the surface sub-images are mosaicked to obtain a mosaicked surface image. An exemplary method to mosaic the surface sub-images is described above.

The method then proceeds to step 1460, where the obtained A-scans are synchronized with the surface sub-images. The synchronization may be performed by making use of the mosaicked surface image, as described above. Synchronization of the A-scans with the surface sub-images allows for determining the location of the A-scans within the surface region. The located A-scans can then be used to derive cross-sectional scan images (B-scans) of a volume behind the TM, as described above. The A-scans can also be used to derive a thickness map of the TM.

In step 1470, the cross-sectional images or the thickness map are segmented to extract a plurality of specified features, as described above. If the cross-sectional images are segmented, the specified features may be features of a volume behind the TM. If the thickness map is segmented, the specified features may be features of the thickness map, i.e. the thickness measurements across the plurality of randomly distributed positions on the surface of the TM.

The method then proceeds to step 1480, where the plurality of specified features is classified. As described in further detail above, the classifier may be a random-forest classifier. As also described above, the output of the classifier characterizes the middle ear fluid, the middle ear biofilm, or both. The classification step may further comprise generating a diagnostic prediction indicating a presence and type of OM as a function of characterizing the middle ear fluid, middle ear biofilm, or both. The method ends at step 1490.

In accordance with certain embodiments of the present invention, aspects of the classification of middle ear abnormalities, described herein, may be implemented as a computer program product for use with a computer system. Such implementations may include a series of computer instructions fixed either on a tangible medium, which is preferably non-transient and substantially immutable, such as a computer readable medium (e.g., a diskette, CD-ROM, ROM, flash drive, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Related teachings may be found in Dsouza et al., "Economical and compact briefcase spectral-domain optical coherence tomography system for primary care and point-of-care applications," J. Biomed. Opt., vol. (Sep. 24, 2018), incorporated herein by reference.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A detector for characterizing at least one of a middle ear fluid and a middle ear biofilm, the detector comprising:
    a handheld probe for directing an output of a broadband source of near-infrared radiation and a source of visible light onto a surface region of a tympanic membrane (TM) within an ear of a human, the handheld probe further comprising a visible light camera;
    an optical coherence tomography (OCT) system adapted to obtain A-scans at a plurality of randomly distributed positions in the surface region as the handheld probe is manually scanned with no lateral scanning mechanism; and
    at least one processor configured to
        (i) concurrently acquire A-scans from the OCT system and visible light surface sub-images of the surface region of the TM from the camera at the plurality of randomly distributed positions, wherein each A-scan is associated with a surface sub-image acquired at the same position, and perform mosaicking of the surface sub-images to obtain a mosaicked surface image in real time;
(ii) synchronize the obtained A-scans with the surface sub-images by making use of the mosaicked surface image and the associations between the A-scans and the surface sub-images to generate a synchronization result selected from the group consisting of three-dimensional scan images of a volume behind the TM within a middle ear space, a three-dimensional thickness map of the TM, and combinations thereof;
(iii) segment the synchronization result to extract a plurality of specified features of the synchronization result; and
(iv) characterize at least one of the middle ear fluid and the middle ear biofilm by classifying the plurality of specified features.

2. The detector of claim 1, wherein the plurality of specified features comprises at least one OCT-derived feature selected from the group consisting of optical thickness, standard deviation of peak-position location, mean of peak width, standard deviation of peak width, mean peak prominence, standard deviation of peak prominence, total number of peaks, optical attenuation maximum, mean value in depth of optical attenuation, attenuation sum over peak-detected depth, Fourier width of central peak, and central Fourier peak prominence.

3. The detector of claim 1, wherein the OCT system comprises a fiber optic Michelson interferometric configuration.

4. The detector of claim 1, wherein the OCT system is selected from the group consisting of a time-domain, spectral-domain, and swept-source OCT system.

5. The detector of claim 1, wherein the classifying is the result of a random-forest classifier.

6. The detector of claim 1, wherein the at least one processor is further configured to generate a diagnostic prediction indicating a presence and type of otitis media as a function of the characterizing the at least one of the middle ear fluid or the middle ear biofilm.

7. The detector of claim 6, wherein the classifying further comprises classifying clinical data of the human together with the plurality of specified features.

8. The detector of claim 1, wherein the at least one processor is further configured to median filter the synchronization result.

9. The detector of claim 1, wherein the mosaicking comprises cross-correlating the surface sub-images.

10. The detector of claim 1, wherein the broadband source of near-infrared radiation has a center wavelength of 840 nm and a bandwidth of 50 nm.

11. A detector comprising:
a handheld probe for directing an output of a broadband source of near-infrared radiation and a source of visible light onto a surface region, the handheld probe further comprising a visible light camera;
an optical coherence tomography (OCT) system adapted to obtain A-scans at a plurality of randomly distributed positions in the surface region as the handheld probe is manually scanned with no lateral scanning mechanism; and a computing device having at least one processor configured to
(i) concurrently acquire A-scans from the OCT system and visible light surface sub-images of the surface region from the camera at the plurality of randomly distributed positions, wherein each A-scan is associated with a surface sub-image acquired at the same position, and perform mosaicking of the surface sub-images to obtain a mosaicked surface image in real time;
(ii) synchronize the obtained A-scans with the surface sub-images by making use of the mosaicked surface image and the associations between the A-scans and the surface sub-images to generate a synchronization result selected from the group consisting of three-dimensional scan images of a volume behind the surface region, a three-dimensional thickness map of the surface region, and combinations thereof.

12. The detector of claim 11, wherein the handheld probe, the OCT system, and the computing device are arranged in a briefcase.

13. The detector of claim 11, wherein the OCT system comprises a spectrometer with a line-scan camera having a line rate of at least 10 kHz.

14. The detector of claim 11, wherein the computing device is a laptop computer.

15. The detector of claim 11, wherein the at least one processor is further configured to:
segment the synchronization result to extract a plurality of specified features of the synchronization result; and
classify the plurality of specified features to characterize at least one of a middle ear fluid and a middle ear biofilm.

16. The detector of claim 15, wherein the plurality of specified features comprises at least one OCT-derived feature selected from the group consisting of optical thickness, standard deviation of peak-position location, mean of peak width, standard deviation of peak width, mean peak prominence, standard deviation of peak prominence, total number of peaks, optical attenuation maximum, mean value in depth of optical attenuation, attenuation sum over peak-detected depth, Fourier width of central peak, and central Fourier peak prominence.

17. The detector of claim 16, further comprising generating a diagnostic prediction indicating a presence and type of otitis media as a function of the characterizing the at least one of the middle ear fluid and the middle ear biofilm.

18. A method for obtaining at least one of real-time three-dimensional images and a thickness map of tissue, the method comprising:
directing output of a broadband source of near-infrared radiation and a source of visible light via a handheld probe onto a surface region of a tympanic membrane (TM) within an ear of a human;
manually scanning the handheld probe to obtain optical coherence tomography (OCT) A-scans at a plurality of randomly distributed positions on the surface region;
concurrently acquiring, by a visible light camera in the handheld probe, surface sub-images of the surface region of the TM at the plurality of randomly distributed positions, wherein each A-scan is associated with a surface sub-image acquired at the same position;
mosaicking the surface sub-images to obtain a mosaicked surface image in real time; and
synchronizing the obtained OCT A-scans with the surface sub-images by making use of the mosaicked surface image and the associations between the A-scans and the surface sub-images to derive a synchronization result selected from the group consisting of three-dimensional scan images of a volume behind the TM within a middle ear space a three-dimensional thickness map of the TM, and combinations thereof.

19. The method of claim 18, wherein the OCT A-scans comprise at least one of time-domain, spectral-domain, and swept-source OCT A-scans.

20. The method of claim 18, further comprising:
segmenting the synchronization result to extract a plurality of specified features of the synchronization result; and
classifying the plurality of specified features to characterize at least one of a middle ear fluid and a middle ear biofilm.

21. The method of claim 20, wherein the plurality of specified features comprises at least one OCT-derived feature selected from the group consisting of optical thickness, standard deviation of peak-position location, mean of peak width, standard deviation of peak width, mean peak prominence, standard deviation of peak prominence, total number of peaks, optical attenuation maximum, mean value in depth of optical attenuation, attenuation sum over peak-detected depth, Fourier width of central peak, and central Fourier peak prominence.

22. The method of claim 20, wherein the classifying is performed by a random-forest classifier.

23. The method of claim 20, further comprising median filtering the synchronization result.

24. The method of claim 20, further comprising generating a diagnostic prediction indicating a presence and type of otitis media as a function of the characterizing the at least one of the middle ear fluid and the middle ear biofilm.

25. The method of claim 24, wherein the classifying further comprises classifying clinical data of the human together with the plurality of specified features.

26. The method of claim 18, wherein the mosaicking comprises cross-correlating the surface sub-images.

27. A detector for detecting at least one of a middle ear biofilm and a middle ear fluid, the detector comprising:

a handheld source of near-infrared radiation for illuminating tissue within an ear of a human;
a visible light camera configured to obtain visible light images at a plurality of randomly distributed positions in the tissue;
a spectral domain optical coherence tomography (OCT) system adapted to obtain three-dimensional scan images of the tissue at the plurality of randomly distributed positions in the tissue by making use of associations between A-scans acquired by the OCT system at one of the plurality of randomly distributed positions and the visible light images acquired at the same position;
a median filter, comprising a square kernel and a lateral window, adapted to filter the three-dimensional scan images of the tissue;
at least one processor adapted to segment the three-dimensional scan images of the tissue and extract a plurality of specified features of the tissue; and
a classifier for identifying at least one of the middle ear biofilm and the middle ear fluid by classifying the plurality of specified features.

28. The detector of claim 27, wherein the plurality of specified features comprises at least one OCT-derived feature selected from the group consisting of optical thickness, standard deviation of peak-position location, mean of peak width, standard deviation of peak width, mean peak prominence, standard deviation of peak prominence, total number of peaks, optical attenuation maximum, mean value in depth of optical attenuation, attenuation over peak-detected depth, Fourier width of central peak, and central Fourier peak prominence.

29. The detector of claim 27, wherein the classifier is a random-forest classifier.

30. The detector of claim 27, wherein the identifying is further based on clinical data of the human together with the plurality of specified features.

* * * * *